United States Patent
Quennesson

(10) Patent No.: US 11,664,115 B2
(45) Date of Patent: May 30, 2023

(54) VOLUMETRIC IMAGING TECHNIQUE FOR MEDICAL IMAGING PROCESSING SYSTEM

(71) Applicant: Braid Health Inc., San Francisco, CA (US)

(72) Inventor: Kevin Quennesson, San Francisco, CA (US)

(73) Assignee: Braid Health Inc., San Francisco, CA (US)

(*) Notice: Subject to any disclaimer, the term of this patent is extended or adjusted under 35 U.S.C. 154(b) by 0 days.

(21) Appl. No.: 17/106,015

(22) Filed: Nov. 27, 2020

(65) Prior Publication Data

US 2021/0166466 A1  Jun. 3, 2021

Related U.S. Application Data

(60) Provisional application No. 62/941,727, filed on Nov. 28, 2019.

(51) Int. Cl.

| | |
|---|---|
| *G06T 15/08* | (2011.01) |
| *G16H 30/40* | (2018.01) |
| *G16H 15/00* | (2018.01) |
| *G06F 40/40* | (2020.01) |
| *G06N 20/00* | (2019.01) |
| *G06T 7/00* | (2017.01) |
| *G16H 50/50* | (2018.01) |

(Continued)

(52) U.S. Cl.
CPC .......... *G16H 30/40* (2018.01); *G06F 21/602* (2013.01); *G06F 40/40* (2020.01); *G06N 20/00* (2019.01); *G06T 3/40* (2013.01); *G06T 7/0012* (2013.01); *G06T 15/04* (2013.01); *G06T 15/08* (2013.01); *G06T 17/20* (2013.01); *G16H 15/00* (2018.01); *G16H 30/20* (2018.01); *G16H 50/50* (2018.01); *H04L 9/3242* (2013.01); *G06T 2207/20081* (2013.01); *G06T 2210/08* (2013.01); *G06T 2210/41* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 2002/0030675 A1* | 3/2002 | Kawai | H04N 13/178 345/204 |
| 2004/0175055 A1* | 9/2004 | Miller | G06T 3/40 382/284 |

(Continued)

OTHER PUBLICATIONS

Kumar, AD Senthil, and T. S. Anandhi. "Multi image integration and Encryption Algorithm for security applications." IECON 2016—42nd Annual Conference of the IEEE Industrial Electronics Society. IEEE, 2016. (Year: 2016).*

(Continued)

*Primary Examiner* — Sultana M Zalalee
(74) *Attorney, Agent, or Firm* — Fenwick & West LLP

(57) ABSTRACT

A medical imaging communication system processes medical images for being transmitted to a client device. The system receives a set of images, each image corresponding to a slice of a three-dimensional object. The system combines a first subset of the images into a first combined image and combines a second subset of the images into a second combined image. The first and second combined image are compressed using a lossless compression algorithm and transmitted to the client device.

19 Claims, 17 Drawing Sheets

(51) Int. Cl.
*G16H 30/20* (2018.01)
*G06F 21/60* (2013.01)
*G06T 3/40* (2006.01)
*G06T 15/04* (2011.01)
*G06T 17/20* (2006.01)
*H04L 9/32* (2006.01)
*G16H 50/20* (2018.01)

(56) References Cited

U.S. PATENT DOCUMENTS

| | | | |
|---|---|---|---|
| 2006/0257016 A1* | 11/2006 | Shioi | H04N 13/139 |
| | | | 382/154 |
| 2007/0274382 A1* | 11/2007 | Hickey | H04N 19/70 |
| | | | 375/240.03 |
| 2009/0102916 A1* | 4/2009 | Saishu | H04N 13/31 |
| | | | 348/54 |
| 2012/0070045 A1 | 3/2012 | Vesper et al. | |
| 2013/0202202 A1* | 8/2013 | Hasu | G06T 5/50 |
| | | | 382/166 |
| 2013/0243076 A1* | 9/2013 | Malladi | H04N 1/646 |
| | | | 375/E7.026 |
| 2014/0092439 A1* | 4/2014 | Krig | G06T 9/001 |
| | | | 358/2.1 |
| 2014/0119624 A1* | 5/2014 | Ehlers | A61B 5/0066 |
| | | | 382/131 |
| 2014/0247869 A1* | 9/2014 | Su | H04N 19/124 |
| | | | 375/240.03 |
| 2015/0015581 A1* | 1/2015 | Lininger | G06T 15/20 |
| | | | 345/426 |
| 2016/0349192 A1* | 12/2016 | Yamakawa | G01N 23/046 |
| 2017/0064282 A1* | 3/2017 | Lo | H04N 13/282 |
| 2017/0186174 A1* | 6/2017 | George | G06T 7/194 |
| 2018/0027250 A1 | 1/2018 | Fram | |
| 2018/0109772 A1* | 4/2018 | Xu | H04N 13/15 |
| 2018/0199902 A1 | 7/2018 | Erhard | |
| 2018/0249183 A1* | 8/2018 | Lindberg | H04N 19/59 |
| 2019/0246875 A1* | 8/2019 | Mizoguchi | A61B 1/0676 |
| 2020/0137351 A1* | 4/2020 | Bai | G06T 3/40 |
| 2020/0175756 A1* | 6/2020 | Crowe | G06T 17/20 |
| 2020/0372699 A1* | 11/2020 | Raposo Subtil | G06T 5/50 |

OTHER PUBLICATIONS

PCT International Search Report and Written Opinion, PCT Application No. PCT/US20/62509, dated Mar. 25, 2021, 17 pages.

PCT Invitation to Pay, PCT Application No. PCT/US20/62509, dated Jan. 27, 2021, 3 pages.

* cited by examiner

VOLUMETRIC IMAGING TECHNIQUE FOR MEDICAL IMAGING PROCESSING SYSTEM

CROSS REFERENCE TO RELATED APPLICATIONS

This application claims the benefit of U.S. Provisional Application No. 62/941,727, filed Nov. 28, 2019, which is incorporated by reference in its entirety.

FIELD OF THE DISCLOSURE

The present disclosure relates to a medical imaging processing system and more specifically to a secure and efficient system for transmitting and manipulating digital medical images.

BACKGROUND

Being able to collaborate in the medical field is beneficial in many ways. By collaborating, medical professionals are able to get opinions about a patient's diagnosis from third parties (such as specialist) to increase the accuracy and quality of the patient's care. Moreover, collaboration enables entities to obtain a larger amount of data for conducting large scale medical studies to further the understanding of various diseases and/or techniques used to treat the diseases. However, while collaboration has many benefits, it is also important to protect patient privacy while sharing the medical information of the patient.

Moreover, with the advancement of technology, client devices are ubiquitous. For example, oftentimes, people have close access to mobile devices for accessing content. However, the use of mobile devices comes with some drawbacks. For instance, mobile devices are limited in power and storage capabilities. Additionally, mobile devices may be limited in bandwidth for transferring data in or out of the mobile device. Furthermore, as the medical technology increases, the amount of data and complexity of the data generated by some medical tests also increases. As such, it would be beneficial to develop an efficient way for allowing a mobile device to consume this medical data as well as present it given the technical constraints of such devices (e.g., relatively small viewing areas, limited processing capabilities and power consumption considerations).

SUMMARY

Embodiments relate to a medical imaging communication system. By way of example, the medical imaging communication system receives medical test packages, processes the medical test packages, stores the medical test packages, and controls the distribution of the medical test packages.

In some embodiments, the medical imaging communication system deidentifies medical test packages for protecting the privacy of patients. The system receives a medical test package. The medical test package includes at least patient identifiable information and one or more medical digital images. The system identifies the patient identifiable information from the received medical test package. The system generates encrypted patient identifiable information by encrypting the patient identifiable information using an encryption key. The system deidentifies the medical test package by replacing the patient identifiable information in the medical test package with the encrypted patient identifiable information. The deidentified medical test package is transmitted to one or more third-party users.

In other embodiments, the medical imaging communication system processes medical images for being transmitted to a client device. The system receives a set of images, each image corresponding to a slice of a three-dimensional object. The system combines a first subset of the images into a first combined image and combines a second subset of the images into a second combined image. The first and second combined image are compressed using a lossless compression algorithm and transmitted to the client device.

In yet other embodiments, the medical imaging communication system generates a graphical user interface for displaying medical test information. The system receives, from a reviewing user, one or more comments for an image, the one or more comments associated with a portion of the image, each comment corresponding to an observation by the reviewing user on the corresponding portion of the image. The system identifies, from each comment, the portion of the image associated with the comment. The system generates an annotated image by overlaying the comment and an indication of the identified portion of the image associated with the comment.

In yet other embodiments, the medical imaging communication system generates an automated report for a medical image corresponding to a patient. The system receives one or more medical images for a patient. The system applies a model to identify an abnormality in the received one or more medical images. The model is configured to determine a likelihood score for the presence of the abnormality in the one or more medical images. If the likelihood score is above a threshold value, the system generates an automated report indicating the type of abnormality identified in the received one or more medical images. The automated report is then provided to a viewing user (e.g., a medical professional viewing the one or more medical images).

BRIEF DESCRIPTION OF THE DRAWINGS

The teachings of the embodiments can be readily understood by considering the following detailed description in conjunction with the accompanying drawings.

FIG.

DETAILED DESCRIPTION

Figure 1:
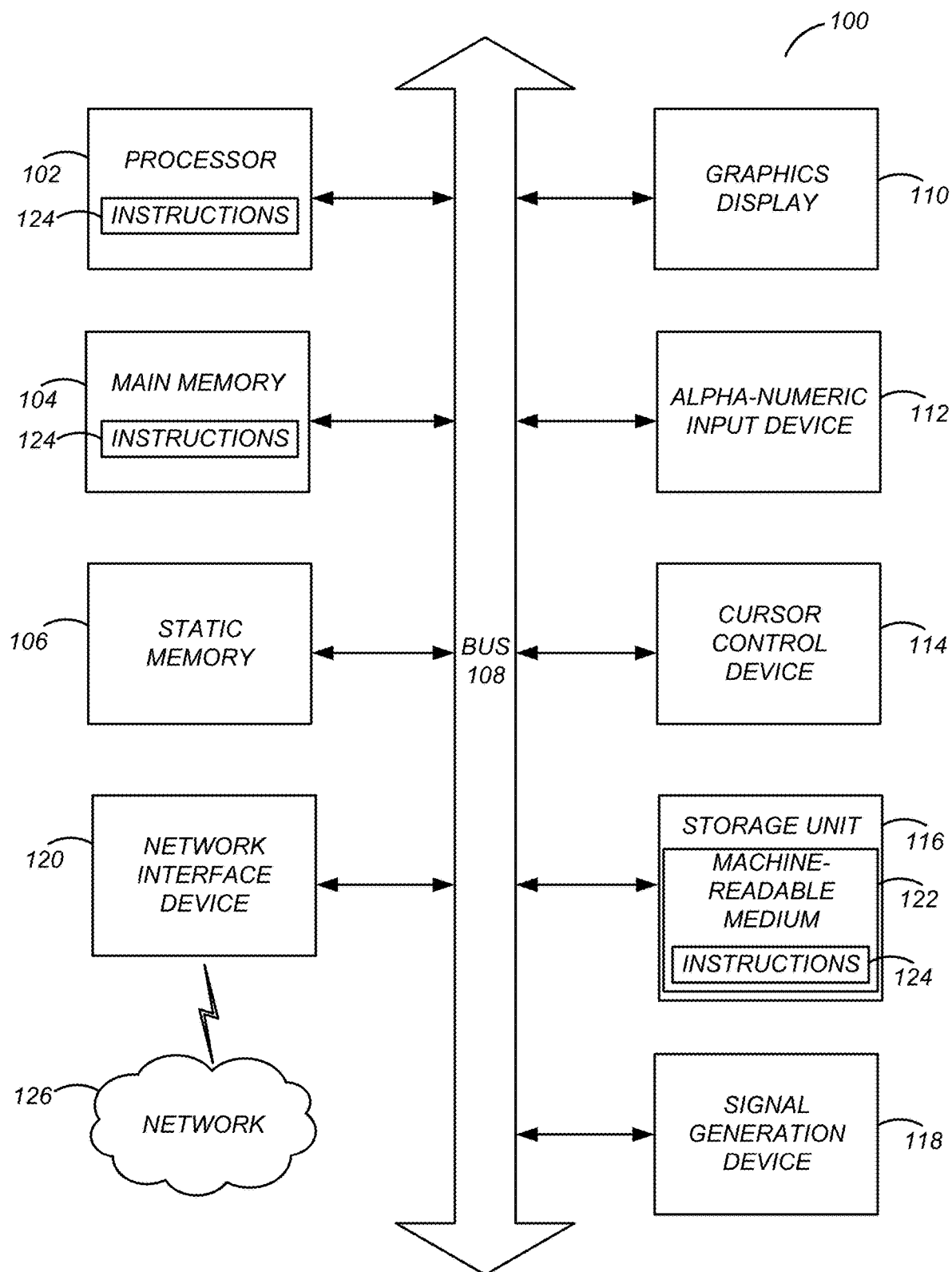
(FIG. 1 is a block diagram illustrating components of an example machine able to read instructions from a machine-readable medium and execute them in a processor (or controller).

The Figures (FIG.) and the following description relate to preferred embodiments by way of illustration only. It should be noted that from the following discussion, alternative embodiments of the structures and methods disclosed herein will be readily recognized as viable alternatives that may be employed without departing from the principles of the embodiments.

Reference will now be made in detail to several embodiments, examples of which are illustrated in the accompanying figures. It is noted that wherever practicable, similar or like reference numbers may be used in the figures and may indicate similar or like functionality. The figures depict embodiments for purposes of illustration only.

Configuration Overview

One embodiment of a disclosed system, method and computer readable storage medium for a medical imaging communication system. The medical imaging communication system receives medical test packages, processes the medical test packages, stores the medical test packages, and controls the distribution of the medical test packages.

In some embodiments, the medical imaging communication system deidentifies medical test packages for protecting the privacy of patients. The system receives a medical test package. The medical test package includes at least patient identifiable information and one or more medical digital images. The system identifies the patient identifiable information from the received medical test package. The system generates an encrypted patient identifiable information by encrypting the identified patient identifiable information using an encryption key. The system deidentifies the medical test package by replacing the patient identifiable information in the medical test package with the encrypted patient identifiable information. The deidentified medical test package is sent to one or more third-party users. Moreover, in some embodiments, the deidentified medical test package is stored in an external storage medium (e.g., using a cloud storage service)

Moreover, the deidentification of the medical test package may include hashing, using a one-way cryptographic hash algorithm, one of a patient identification (patient ID) or a study identification (study ID) from the received medical test package to generate a hashed identification. The hashed identification is then inserted to the deidentified medical test package to enable users to match multiple deidentified medical test packages to each other.

In one embodiment, the encrypted patient identifiable information is unable to be decrypted without a decryption key. Additionally, in one embodiment, the patient identifiable information includes the patient's personal identifiable information (PII) such as a patient's name.

In one embodiment, the one or more third-party users include a collaborator for providing a report including an analysis for the one or more medical digital images included in the deidentified medical test package.

In one embodiment, the one or more third-party users include an entity conducting a medical study.

In one embodiment, deidentified medical test package is sent to the one or more third-party users using the Digital Imaging and Communication in Medicine (DICOM) standard.

Moreover, in some embodiments, the deidentified medical test package is received at a client device. The client device then retrieves a decryption key for decrypting the encrypted patient identifiable information. The client device identifies the encrypted patient identifiable information from the deidentified medical test package and decrypts the identified encrypted patient identifiable information. If the decryption is successful, the client device displays the decrypted patient identifiable information and the one or more medical digital images from the deidentified medical test package. In one embodiment, the decryption key is stored in a secure location of the client device. For example, the decryption key is installed in the secure location of the client device by a system administrator of a health care institution associated with the decryption key.

Alternatively, in one embodiment, the deidentified medical test package is received at a client device. The client device then determines if a decryption key for decrypting the encrypted patient identifiable information is available. If the decryption key is not available, the client device displays the one or more medical digital images as being attributed to an anonymous patient. Otherwise, if the decryption key is available, the client device decrypts the identified encrypted patient identifiable information, and displays the decrypted patient identifiable information and the one or more medical digital images from the deidentified medical test package.

In one embodiment, to determine whether decryption key for decrypting the encrypted patient identifiable information is available, the client device retrieves a potential decryption key and attempts to decrypt the encrypted patient identifiable information using the potential decryption key. If the decryption attempt fails, the client device determines that the decryption key is unavailable.

For example, in attempting to decrypt the encrypted patient identifiable information using the potential decryption key, the client device performs a decryption operation on the encrypted patient identifiable information using the potential decryption key to generate a decrypted value. If the resulting decrypted value does not match a predetermined format, the client device determines that the decryption failed. For instance, the client device may compare a digest of the decrypted value to an expected digest for the encrypted patient identifiable information. If the two digests do not match, the client device determines that the potential decryption key is not the decrepitation key for decrypting the encrypted patient identifiable information.

In other embodiments, the medical imaging communication system processes medical images for being transmitted to a client device. The system receives a set of images, each image corresponding to a slice of a three-dimensional object. The system combines a first subset of the images into a first combined image and combines a second subset of the images into a second combined image. The first and second combined image are compressed using a lossless compression algorithm and sent to the client device.

In one embodiment, the first combined image is generated by arranging each pixel of each image of the first subset of images into the first combined image. In one embodiment, the first combined image is generated by interlacing the images in the first subset of images.

In one embodiment, the images in the set of images have a first bit depth. Moreover, the images in first subset of images are combined into a third combined image. The first combined image and the third combined image have a second bit depth, the second bit depth lower than the first bit depth.

In one embodiment, for each pixel of each image in the first subset of images, a location associated with the pixel in the first combined image is determined, a new pixel having the second bit depth from the pixel having the first bit depth is determined, and the new pixel is stored in the first combined image at the determined location associated with the pixel.

In one embodiment, the set of images are medical images captured using a medical imaging device. In one embodiment, the medical imaging device is one of a computer tomography (CT) scanner, a magnetic resonance imaging (MRI) scanner, an X-ray machine, and an ultrasound machine.

In one embodiment, the set of images are received using the Digital Imaging and Communication in Medicine (DICOM) standard.

In one embodiment, a slice is a two-dimensional image of the three-dimensional object across a specific plane at a specific depth In yet other embodiments, the medical imaging communication system generates a graphical user interface (GUI) that is provided (or enabled) to display medical test information on a screen of a computing device. The system receives, from a reviewing user, one or more comments for an image, the one or more comments associated with a portion of the image, each comment corresponding to an observation by the reviewing user on the corresponding portion of the image. The system identifies, from each comment, the portion of the image associated with the comment. The system generates an annotated image by overlaying the comment and an indication of the identified portion of the image associated with the comment. In one embodiment, the system further generates a web page. The web page may include at least the annotated image and the received one or more comments for an image In one embodiment, to identify the portion of the image associated with the comment, a description of a location within the image is identified from the one or more comments.

In one embodiment, the description of the location within the image is identified by applying a trained natural language processing (NLP) model to the one or more comments for the image.

In one embodiment, the NLP model is trained using a machine learning algorithm and a training set. The training set includes a plurality of labeled comments, each labeled comment of the plurality of labeled comments indicating a portion of the labeled comment corresponding to a description of a location.

In one embodiment, to identify the portion of the image associated with the comment, a trained image recognition model is applied to identify one or more objects included in the identified description of the location within the image.

In one embodiment, the image recognition model is trained using a machine learning algorithm and a training set. The training set includes a plurality of labeled images, each labeled image of the plurality of labeled images including a description of location within the image and an indication of the location corresponding to the description.

In yet other embodiments, the medical imaging communication system generates an automated report for a medical image corresponding to a patient. The system receives one or more medical images for a patient. The system applies a model to identify an abnormality in the received one or more medical images. The model is configured to determine a likelihood score for the presence of the abnormality in the one or more medical images. If the likelihood score is above a threshold value, the system generates an automated report indicating the type of abnormality identified in the received one or more medical images. The automated report is then provided to a viewing user (e.g., a medical professional viewing the one or more medical images).

In one embodiment, to apply a model to determine the likelihood score, an image recognition model is first applied to the one or more medical images to determine a type of object depicted in the one or more medical images. Based on the type of object depicted, one or more abnormality detection models corresponding to the determined type of object are identified. Each abnormality detection model is trained to detect one or more types of abnormalities for the determined type of object depicted in the one or more medical images.

In one embodiment, prior to applying a model to determine the likelihood score, one or more comments for the medical image are received from a reviewing user. Each comment corresponds to an observation by the reviewing user of the image. Natural language processing is then applied to the one or more comments to identify a potential abnormality observed by the reviewing user. Based on the outcome of the natural language processing model, one or more abnormality detection models corresponding to the identified potential abnormality are identified.

In one embodiment, a modification for the generated automated report is received from the viewing user. Based on the received modification, the models applied to the one or more medical images are retrained.

Computing Machine Architecture

FIG. (FIG. 1 is a block diagram illustrating components of an example machine able to read instructions from a machine-readable medium and execute them in a processor (or controller). Specifically, FIG. 1 shows a diagrammatic representation of a machine in the example form of a computer system 100 within which instructions 124 (e.g., software or program code) that when executed caused the machine to perform any one or more of the methodologies discussed herein. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 124 (sequential or otherwise) that specify actions to be taken by that machine. Further, while only a single machine is illustrated, the term "machine" shall also be taken to include any collection of machines that individually or jointly execute instructions 124 to perform any one or more of the methodologies discussed herein.

The example computer system 100 includes a processor 102 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 104, and a static memory 106, which are configured to communicate with each other via a bus 108. The computer system 100 may further include graphics display unit 110 (e.g., a plasma display panel (PDP), a liquid crystal display (LCD), a projector, or a cathode ray tube (CRT)). The computer system 100 may also include alphanumeric input device 112 (e.g., a keyboard), a cursor control device 114 (e.g., a mouse, a trackball, a joystick, a motion sensor, or other pointing instrument), a storage unit 116, a signal generation device 118 (e.g., a speaker), and a network interface device 820, which also are configured to communicate via the bus 108.

The storage unit 116 includes a machine-readable medium 122 on which is stored instructions 124 (e.g., software) embodying any one or more of the methodologies or functions described herein. The instructions 124 may also reside, completely or at least partially, within the main memory 104 or within the processor 102 (e.g., within a processor's cache memory) during execution thereof by the computer system 100, the main memory 104 and the processor 102 also constituting machine-readable media. The instructions 124 (e.g., software) may be transmitted or received over a network 126 via the network interface device 120.

While machine-readable medium 122 is shown in an example embodiment to be a single medium, the term "machine-readable medium" should be taken to include a single medium or multiple media (e.g., a centralized or distributed database, or associated caches and servers) able to store instructions (e.g., instructions 124). The term "machine-readable medium" shall also be taken to include any medium that is capable of storing instructions (e.g., instructions 124) for execution by the machine and that cause the machine to perform any one or more of the methodologies disclosed herein. The term "machine-readable medium" includes, but not be limited to, data repositories in the form of solid-state memories, optical media, and magnetic media.

System Architecture

Figure 2:
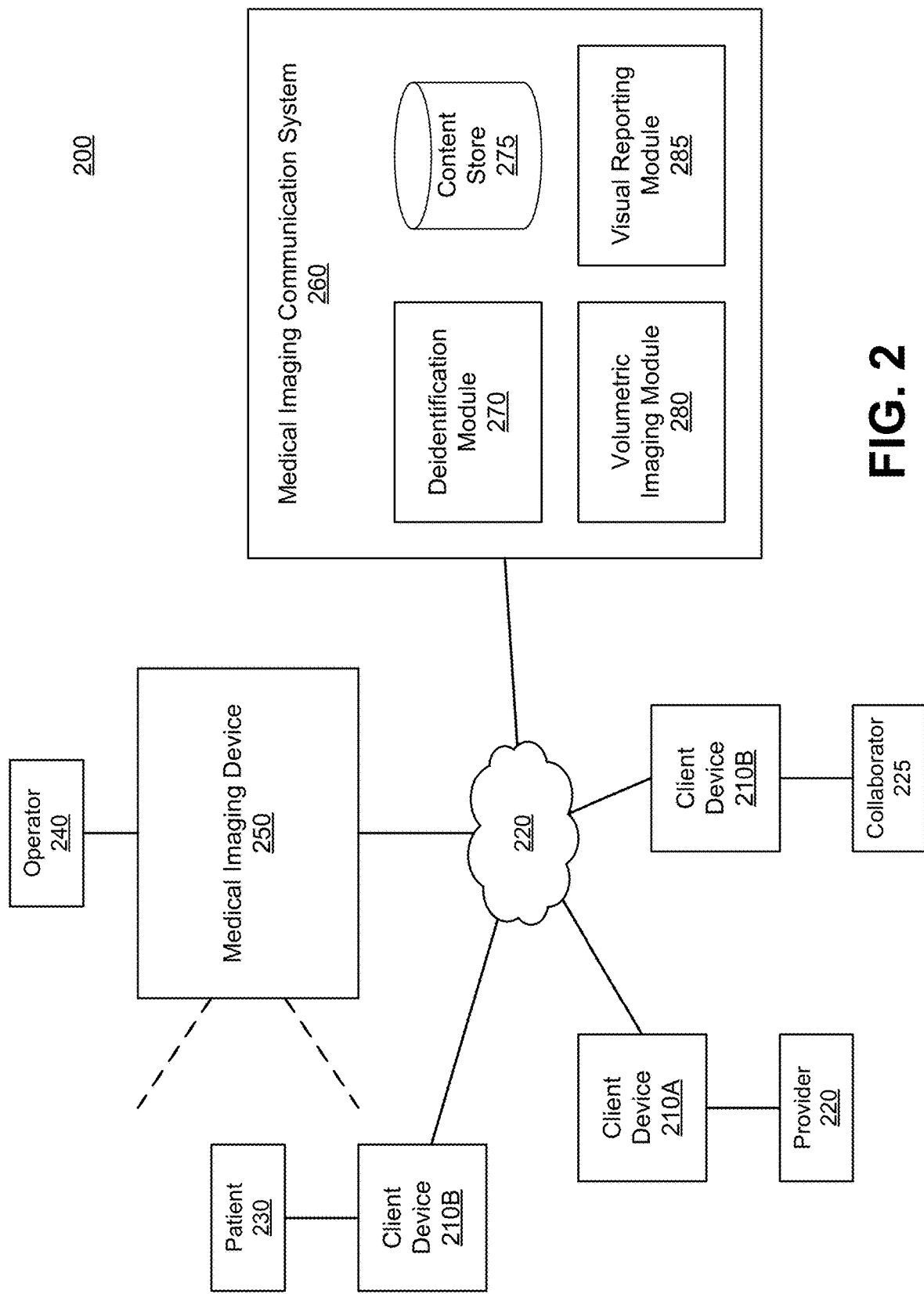
FIG. 2 illustrates a system architecture of a medical imaging communication system, according to one embodiment.

FIG. 2 illustrates a system architecture 200 of a medical imaging communication system 260, according to one embodiment. The medical imaging communication system 260 may be accessed by multiple medical professionals (e.g., doctors or physicians, surgeons, nurses, technicians, and administrators), as well as patients and third-party entities (e.g., scientists or third-party doctors conducting large scale scientific or medical studies).

The system architecture 200 includes the medical imaging communication system 260, a medical imaging device 250, and multiple client devices 210. The client devices are used by various entities accessing the medical imaging communication system 260 to access or manipulate the information stored in the medical imaging communication system 260. For example, a medical provider 220 uses a first client device 210A to access medical images corresponding to a patient 230 to provide a diagnosis for the patient 230. A collaborator 225, such as a specialist or third-party doctor, uses a second client device 210B to access the medical images corresponding to the patient 230 to provide comments on the images for the doctor's consideration, or to use the images in a large-scale medical study. The information accessed by the collaborator may be deidentified to protect the privacy of the patient 230. For example, the personal identifiable information (PII) of the patient is removed from the information available to the collaborator in a way that the collaborator can provide meaningful comments on the medical images without being able to determine which patient the medical images relate to. Moreover, the patient 230 may also be able to access the medical imaging communication system 260. For instance, the patient 230 is able to access his or her own medical images for his or her own records.

The client devices 210 are one or more computing devices capable of receiving user input as well as transmitting and/or receiving data via the network 220. In one embodiment, a client device 210 is a conventional computer system, such as a desktop or a laptop computer. Alternatively, a client device 210 may be a device having computer functionality, such as a personal digital assistant (PDA), a mobile telephone, a smartphone, or another suitable device. A client device 210 is configured to communicate via the network 220. In one embodiment, a client device 210 executes an application allowing a user of the client device 210 to interact with the medical imaging communication system 260. For example, a client device 210 executes a browser application to enable interaction between the client device 210 and the medical imaging communication system 260 via the network 220. In another embodiment, a client device 210 interacts with the medical imaging communication system 260 through an application programming interface (API) running on a native operating system of the client device 210, such as IOS® or ANDROID™.

The client devices 210 are configured to communicate via the network 220, which may comprise any combination of local area and/or wide area networks, using both wired and/or wireless communication systems. In one embodiment, the network 220 uses standard communications technologies and/or protocols. For example, the network 220 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 220 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 220 may be represented using any suitable format, such as hypertext markup language (HTML) or extensible markup language (XML). In some embodiments, all or some of the communication links of the network 220 may be encrypted using any suitable technique or techniques.

The medical imaging device 250 captures medical images and provides the medical images to the medical imaging communication system 260 for storage. For example, the medical imaging device 250 is a computerized tomography (CT) imaging system that produces 2-dimensional images of a "slice" or cross-section of the body of the patient 230. In another example, the medical imaging device 250 is a magnetic resonance imaging (MM) system, an ultrasound (US) system, an X-Ray system, a digital radiography (DX)

system, a computerized radiography (CR) system, an electrocardiography (ECG) system, or any other suitable medical imaging device.

In some embodiments, the medical imaging device 250 is operated by an operator 240. For example, the operator 240 may be a technician or a radiologist. The operator 240 operates the medical imaging device 250 according to instructions provided by the medical provider 220 of the patient 230. The operator 240 further accesses the medical imaging communication system 260 (e.g., through the medical imaging device) to store the medical images captured by the medical imaging device 250.

The medical imaging device 250 communicates with the medical imaging communication system 260 using a specified communication standard. For example, the medical imaging device 250 uses the Digital Imaging and Communication in Medicine (DICOM) standard. The medical imaging device 250 formats the patient medical images and the patient data in a DICOM file as specified by the DICOM standard, and transmits the DICOM file to the medical imaging communication system 260.

Medical Imaging and Communication System

The medical imaging communication system 260 receives patient medical images and patient data from various sources and stores the received data securely. In some embodiments, the medical imaging communication system 260 further controls access to the patient information and prevents unauthorized entities from accessing sensitive patient information. The medical imaging communication system 260 may include, among other components, a deidentification module 270, and a content store 275, a volumetric imaging module 280, a visual reporting module 285. The functionality of each module may be embodied as instructions and may be stored in a storage, e.g., main memory 104 and/or storage unit 116, and executable by a processor, e.g., processor 102. The functionality of each module also may be embodied in application specific integrated circuits (ASICs) and/or field programmable gate arrays (FPGAs).

Although in the example of FIG. 2, the medical imaging communication system 260 is shown as a single system, the medical imaging communication system 260 may be a decentralized system, or may be composed of multiple independent systems. For example, the content store 275 may be a decentralized cloud storing system. Additionally, one or more components shown in FIG. 2 as being part of the medical imaging communication system 260 may be instead implemented in each of the client devices connected via the network 220. For example, instead of having a centralized deidentification module 270, each client device 210 (or a subset thereof) and/or the medical imaging device 250 may locally implement an instance of the deidentification module 270 such that the functions of the deidentification module 270 are performed in a decentralized fashion in each client device 210.

A. Patient Deidentification

Figure 3:
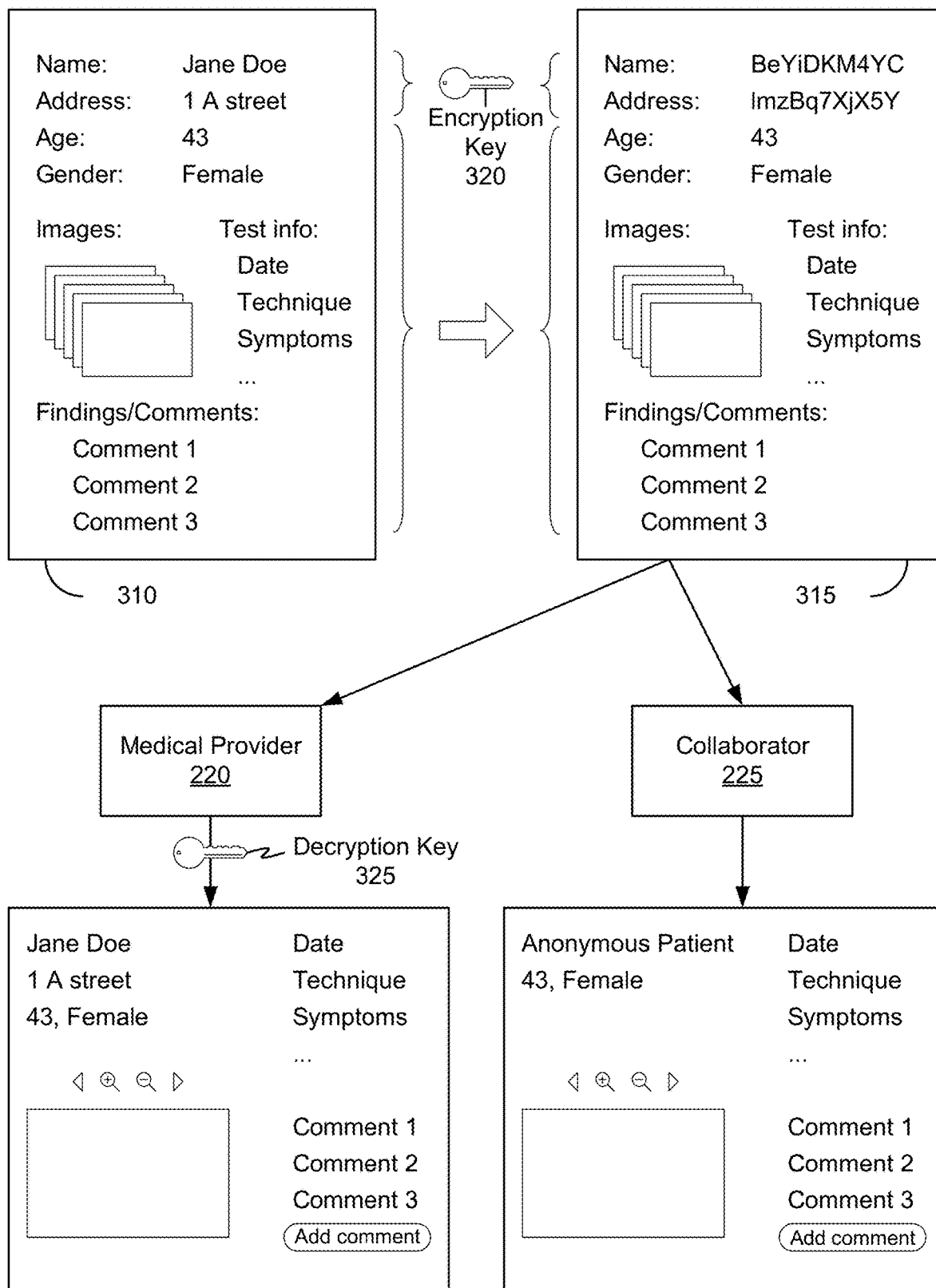
FIG. 3 illustrates a system environment for the deidentification of medical test packages, according to one embodiment.

The deidentification module 270 receives a medical test package and removes personal identifiable information (PII) prior to storing the medical test package in the store 275. For example, the medical test package may be a file containing medical images and formatted using a format compliant with the DICOM standard. FIG. 3 illustrates a system environment for the deidentification of medical test packages 310, according to one embodiment.

The deidentification module 270 deidentifies (e.g., anonymizes) medical test packages 310 received from a medical imaging device 250. In some embodiments, the deidentification module 270 is further configured to deidentify other types of patient information to remove PII related to the patient before being stored in content store 275 or being distributed to client devices 210B of collaborators 225.

A patient's medical test package 310 includes patient information (e.g., patient's name, patient's address, patient's identification number, patient's age, patient's gender, etc.), test information (e.g., test date, test duration, test technique, test parameters, patient's symptoms, etc.), one or more test results (e.g., one or more medical images (such as CT scans, CAT scans, MRI scans, X-Rays, ultrasounds, etc.), one or more analytical test results, etc.), and one or more comments or findings. In some embodiments, the patient's medical test package 310 includes additional information (e.g., operator/technician information, test location information, etc.).

The medical test package 310 may be provided to the medical imaging communication system 260 for storage from the medical imaging device 250. The medical test package 310 is formatted with a predetermined format. The medical test package 310 may be transmitted to the medical imaging communication system 260 in an encrypted form to protect the patient's privacy.

To deidentify the medical test package 310, the deidentification module 270 uses an encryption key 320 to modify the patient PII before storing the deidentified medical test package 315. As such, without a decryption key 325 that corresponds to the encryption key 320, an entity is unable to obtain the patient PII from the stored deidentified medical test package 315. In some embodiments, the deidentification module 270 identifies which portion of the medical test package 310 contains patient's PII and encrypts the identified portions. For example, the deidentification module 270 identifies portions of the patient's information (such as patient's name, patient's address, and patient's identification number) and replaces the identified patient's PII with an encrypted version of the patient's PII. As a result, the deidentified medical test package 315 includes the encrypted version of the patient's PII and unencrypted version (or plaintext version) of the non-PII information.

In some embodiments, the deidentification module 270 uses symmetric encryption, where the encryption key is kept secret and may be used for both encrypting and decrypting the patient PII to deidentify a patient's medical test package. As such, an entity that has the encryption key is able to decrypt the patient PII to determine which patient the medical test package 310 corresponds to.

In other embodiments, the deidentification module 270 uses asymmetric encryption, where an encryption key might be made public to allow any entity to use the encryption key to encrypt the patient PII. For instance, if a first entity wants to share a patient's medical test package 310 with a second entity in a way that the second entity is able to determine the identity of the patient, the first entity can deidentify the patient's medical test package 310 using the second entity's encryption key. That way, if the second entity's decryption key is kept secret, entities other than the second entity that do not have access to the second entity's decryption key are unable to determine the identity of patient.

In some embodiments, each entity (or entity group) has their own encryption key 320 and decryption key 325. For example, each hospital or practice group may have their own encryption key 320 and decryption key 325. As such, medical providers affiliated with the hospital or practice group are able to determine the identity of the patient associated with the medical test package 310 to be able to provide the results and findings of the test to the patient. In some embodiments, the decryption keys 325 are stored in a secure location within client devices of users that are authorized to have the decryption keys 325. For instance, the decryption keys 325 for a health care institution (e.g., a hospital) may be stored in client devices assigned to medical professionals affiliated with the health care institution (e.g., configured by a system administrator). Alternatively, the decryption keys 325 are stored in the medical imaging communication system 260 and they are able to be accessed after a user has been authenticated by the medical imaging communication system 260.

In some embodiments, the deidentification module 270 of a first entity (e.g., the deidentification module 270 of an imaging center) accesses an encryption key 320 that is stored in a client device of a second entity (e.g., the client device owned by a hospital), and deidentifies the medical test package 310 using the entity's encryption key 320. In another embodiment, the deidentification module 270 locally stores the encryption key 320 for the entity and deidentifies the medical test package using the stored encryption key 320.

For example, the deidentification module 270 of a hospital's medical imaging communication system 260 stores the encryption key 320 associated with the hospital. As such, upon receipt of a new medical test package 310 for a patient of the hospital, the deidentification module 270 deidentifies the medical test package 310 to generate the deidentified medical test package 315, and stores the deidentified medical test package 315 in the content store 275.

In some embodiments, the medical imaging device 250 performs the deidentification prior to sending the medical test packages 310 to the medical imaging communication system 260. For instance, the medical imaging device 250 may have an encryption key 320 stored therein, or may retrieve the encryption key 320 from the medical imaging communication system 260.

In yet other embodiments, when the medical image is captured by a third-party entity (e.g., when the patient is referred to a medical imaging center by the patient's medical provider), the third-party entity deidentifies the patient's medical test package using the patient's medical provider's encryption key 320 prior to transmitting the medical test package 310 to the medical imaging communication system 260 of the patient's medical provider. In some embodiment, the third-party medical imaging center has its own medical imaging communication system 260 that is capable of communication with the patient's medical provider's medical imaging communication system 260. Since the medical imaging center deidentified the medical test package 310 using the medical provider's encryption key 320, the medical provider is able to decrypt the encrypted portions of the deidentified medical test package 315 to determine the identity of the patient.

When a medical provider 220 accesses the medical imaging communication system 260 to retrieve a patient's medical test package 310, the medical provider 220 retrieves the deidentified medical test package 315 from the medical imaging communication system 260 and decrypts the deidentified medical test package 315 using the decryption key 325. In some embodiments, the decryption of the encrypted portions of the deidentified medical test package 315 is performed in the medical provider's client device 210. In other embodiments, the decryption of the encrypted portions of the deidentified medical test package 315 is performed by the deidentification module 270 of the medical imaging communication system 260 after determining that the medical provider is authorized to access the patient's PII (e.g., by verifying the medical provider's credentials or by authenticating an online session of the medical provider).

In some embodiments, the medical provider 220 is able to browse the available medical test packages 310 stored in the medical imaging communication system 260. Since the medical provider 220 has access to the decryption key 325, while browsing the available medical test packages 310, the medical provider 220 is able to retrieve the patients' PII from each of the medical test packages 310.

In some embodiments, collaborators 225 are able to access one or more deidentified medical test packages 315 stored in the medical imaging communication system 260. For instance, a collaborator 225 may be a specialist asked to provide an opinion on a possible diagnosis for a patient based on the information available in the deidentified medical test package 315. In order to provide an opinion, the collaborator 225 is able to access the unencrypted portions of the deidentified medical test package 315. However, since the collaborator 225 does not have a decryption key 325 corresponding to the encryption key 320 used to deidentify the medical test package 310, the collaborator 225 is unable to decrypt the encrypted portions of the deidentified medical test packages 315. As such, the collaborator 225 may see the medical test package as corresponding to an anonymous patient.

In some embodiments, the collaborator 225 accesses the deidentified medical test packages 315 through the collaborator's medical imaging communication system 260. The collaborator's medical imaging communication system 260 is able to communicate with the provider's medical imaging communication system 260 to retrieve the deidentified medical test packages 315 and store the deidentified medical test packages 315. However, since the collaborator's medical imaging communication system 260 does not have the provider's decryption key 325, the collaborator's medical imaging communication system 260 is unable to decrypt the encrypted portions of the deidentified medical test packages 315.

As such, entities that have access to the decryption key (private key access), such as health professionals within a patient's healthcare institution, are able to decrypt the medical test package and access the information as if the medical test package was never deidentified. However, entities that do not have access to the decryption key are only able to access the deidentified data or the unencrypted portion of the deidentified medical test package.

By deidentifying the medical test packages as described above, the deidentified medical test packages can be safely stored or backed up in an external location (e.g., in the cloud), without exposing patient's sensitive personal identifiable information. That is, prior to pushing the medical test package to an external storage device, the medical test package is deidentified to prevent unauthorized access to patients' PII. Moreover, the deidentification of medical test packages enables medical professionals to collaborate to get opinions and diagnosis without sharing a patient's identifiable health data. Additionally, the described deidentification scheme allows the process to be transparent to health professionals that have the clearance or authorization to access the patient's identifying information.

In some embodiments, certain fields (such as patient IDs and study IDs) are hashed (e.g., using SHA256) through an irreversible one-way transformation. This allows studies and patients to be matched by accessing the deidentified data without having to decrypt the encrypted portion of the deidentified medical test package. That is, this allows studies and patients to be matched by simply looking at the unencrypted portion of the deidentified medical test package.

Figure 4:
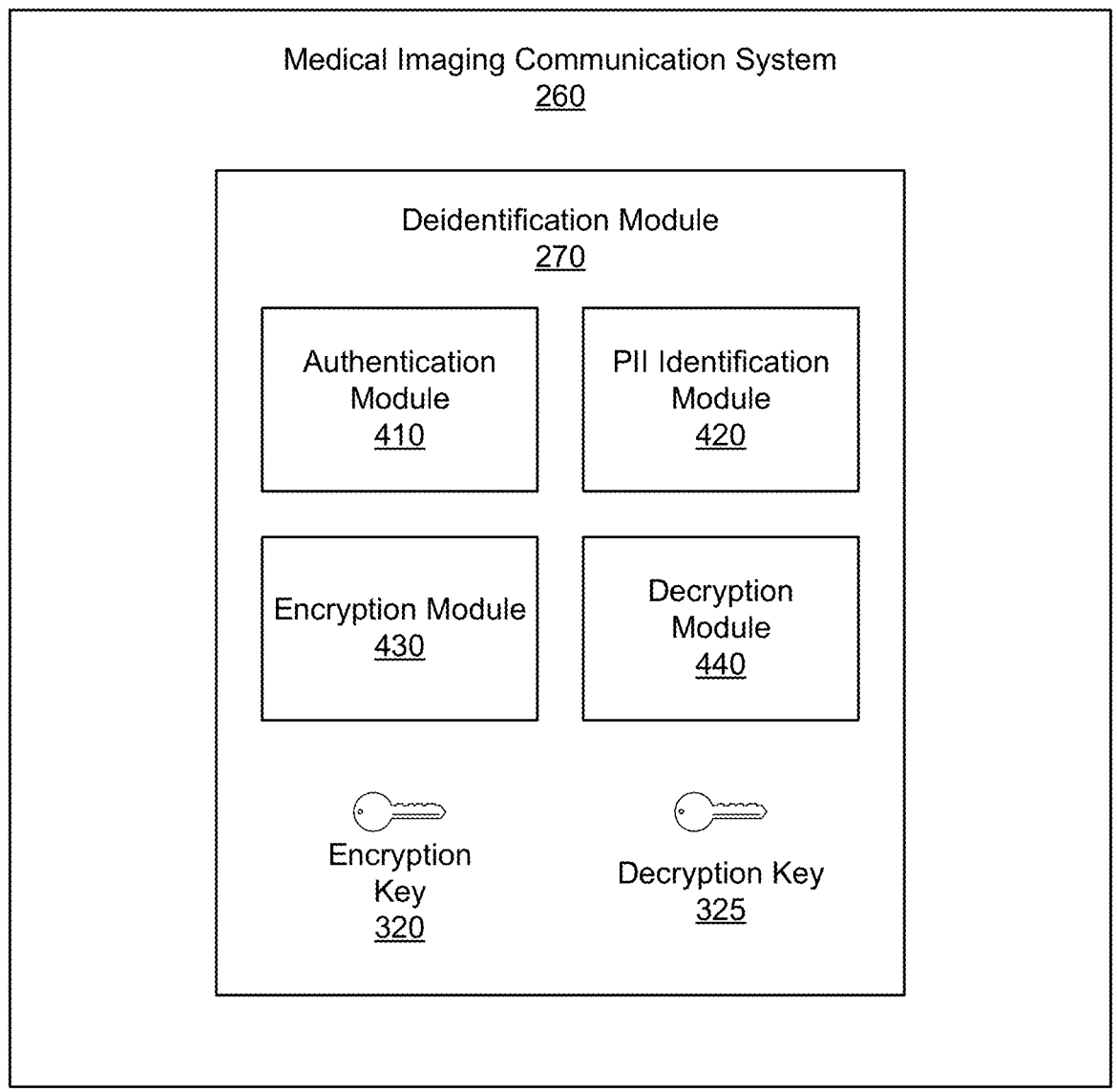
FIG. 4 illustrates a block diagram of the deidentification module of the medical imaging communication system, according to one embodiment.

FIG. 4 illustrates a block diagram of the deidentification module 270 of the medical imaging communication system 260, according to one embodiment. The deidentification module 270 includes an authentication module 410, a personal identifiable information (PII) identification module 420, an encryption module 430, and a decryption module 440. In some embodiments, the deidentification module 270 may include additional or fewer elements than the ones depicted in FIG. 4. Moreover, in some embodiments, the elements shown in FIG. 4 may be distributed among more than one system. For example, the encryption module 430 and the decryption module 440 may be implemented in different computing systems.

The authentication module 410 authenticates a user of the medical imaging communication system 260. In some embodiments, the authentication module 410 authenticates a user based on a username and password provided by the user. In other embodiments, the authentication module 410 uses biometric data to authenticate users of the medical imaging communication system 260. In yet other embodiments, the authentication module 410 uses multi-factor authentication to authenticate users of the medical imaging communication system 260. In yet other embodiments, the authentication module 410 relies on an operating system level authentication based on the operating system of a client device connecting to the medical imaging communication system 260.

The PII identification module 420 receives a medical test package 310 and identifies a patient's PII from the medical test package 310. In some embodiments, the PII identification module 420 parses through the medical test package 310 and identifies pre-set fields that correspond to PII information. For example, the PII identification module 420 identifies a name field as containing a patient's PII.

In some embodiments, the PII identification module 420 uses a set of rules for determining whether a piece of information is PII. For example, the PII identification module determines whether a field contains PII based on the name of the field. For instance, if the name of the field is "address," the PII identification module 420 identifies the information contained in that field as PII. Alternatively, the PII identification module 420 compares the content included in the medical test package 310 to the corresponding patient's known PII. If the PII identification module 420 finds a match, the PII identification module 420 identifies the matching information as PII. For instance, after scanning the information included in the medical test package 310, the PII identification module 420 determines that the words "Jane Doe" matches the name of the corresponding patient. In this case, the PII identification module 420 identifies the words "Jane Doe" as PII.

In some embodiments, the PII identification module 420 additionally applies a trained model (in addition to or instead of identifying pre-set fields) to identify a patient's PII. For example, the PII identification module 420 trains a classifier module to identify PII based on labeled data that species portions of medical test packages as containing a patient's PII.

The encryption module 430 encrypts the identified PII from a medical test package 310 to generate a deidentified medical test package 315. The encryption module 430 uses an encryption key 320 to deidentify the medical test package 310. In some embodiments, the deidentification module 270 locally stores the encryption key 320. In other embodiments, the deidentification module 270 requests the encryption key from a computing device of the user providing the medical test package 310. In other embodiments, a user providing the medical test package 310 may select the encryption key to use for deidentifying a medical test package 310. For instance, an operator of a medical imaging device (e.g., from a third-party medical imaging center) may specify to use an encryption key corresponding to the patient's medical provider. As such, the encryption module 430 communicates with the medical imaging communication system 260 of the patient's medical provider and retrieves the patient's medical provider's encryption key 320.

The decryption module 440 decrypts the encrypted portions of a deidentified medical test package 315. The decryption module 440 uses a decryption key 325 to decrypt the encrypted portions of the deidentified medical test package 315. The decryption key 325 is stored locally by the deidentification module 270 and is kept secret. In some embodiments, the decryption key 325 and the encryption key 320 are the same. In this embodiment, the encryption key 320 is also stored locally and kept secret. In other embodiments, the decryption key 325 is different than the encryption key 320. Moreover, the decryption key 325 and the encryption key 320 are generated in a way that prevents a third party from deriving one from the other. As such, the encryption key 320 may be shared with third parties to allow third parties to deidentify medical test packages using the encryption key 320.

Additionally, the encryption key 320 may be used to authenticate the deidentified medical test package 314. In particular, the deidentification module 270 may sign the deidentified medical test package 315 using the decryption key 325. The signature included in the deidentified medical test package 315 can then be verified using the corresponding encryption key 320.

In some embodiments, the authentication of the deidentified medical test packages 315 can be used to prevent third parties from tampering with the information included in the deidentified medical test packages 315. For instance, a malicious third party may attempt to modify an unencrypted portion of the deidentified medical test packages 315 (e.g., by modifying a medical image included in the deidentified medical test packages 315). Using the authenticating process, since the third party will be unable to authenticate ownership of the deidentified medical test packages 315, the third party may be prevented from making the unauthorized modification.

Alternatively, the authentication process may be used to detect tampering of the deidentified medical test packages 315. If a third party maliciously modifies the deidentified medical test packages 315, the owner of the deidentified medical test packages 315 may prove ownership of the deidentified medical test packages 315 using a digital signature and may provide the correct information to revert the changes made by the third party.

Figure 5:
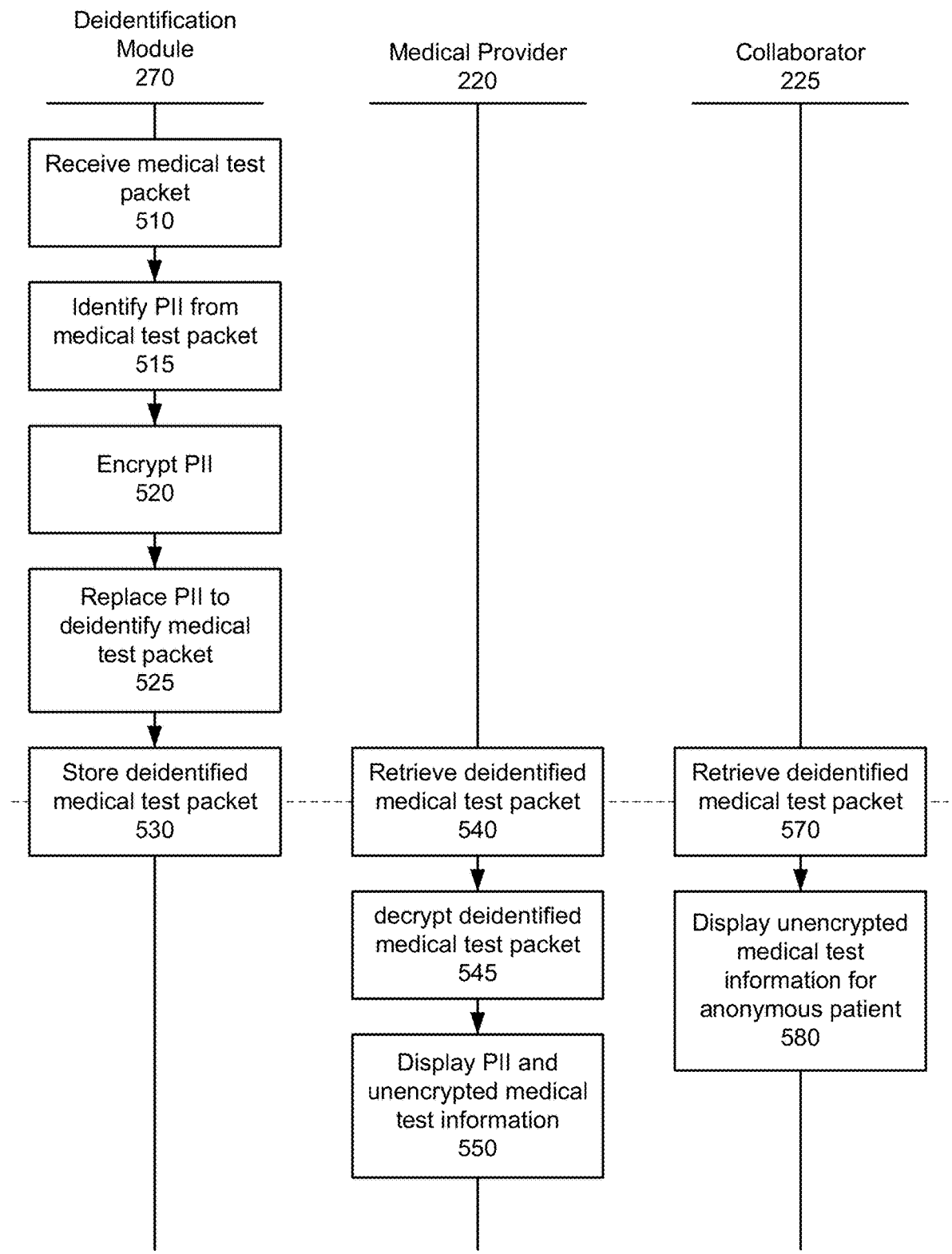
FIG. 5 illustrates a flow diagram of a process for deidentifying medical test packages, according to one embodiment.

FIG. 5 illustrates a flow diagram of a process for deidentifying medical test packages 310, according to one embodiment. The deidentification module 270 receives 510 a medical test package 310. For example, the deidentification module 270 receives the medical test package 310 from the medical imaging device 250. In some embodiments, the medical test package 310 is formatted according to a predetermined standard (e.g., according to the DICOM standard). The received medical test package 310 includes patient's personal identifiable information (PII), patient's non-identifiable information, and test results (e.g., medical images).

The PII identification module 420 identifies 515 patient PII information from the received medical test package 310. The encryption module 430 encrypts 520 the identified patient PII information. The encryption module 430 replaces the patient PII information in the medical test package 310 with the encrypted patient PII information to generate the deidentified medical test package 315. In some embodiments, each PII field is independently encrypted and replaced. In other embodiments, the medical test package 310 is split into two portions, one containing all of the patient PII information. In this embodiment, the portion of the medical test package 310 containing all of the patient PII is encrypted as a single block of data.

The deidentified medical test package 315 is stored 530 in the content store 275 of the medical imaging communication system 260. As such, entities with access to the content store 275 or the medical imaging communication system 260 may retrieve the deidentified medical test package 315.

For example, the patient's medical provider 220 retrieves 540 the deidentified medical test package 315. Since the medical provider 220 has access to the decryption key 325 (e.g., either by retrieving the decryption key 325 from a secure location within the client device 210 of the medical provider 220, or by having authorization to use the decryption key 325 through the medical imaging communication system 260 after having been authenticated by the medical imaging communication system 260), the medical provider 220 is able to decrypt the deidentified medical test package 315. Thus, the medical provider decrypts 545 the deidentified medical test package 315 using the decryption key 325 and displays 550 the unencrypted portion of the medical test package 310 (e.g., test information and test results) as well as the decrypted patient PII information.

In another example, a collaborator 225 retrieves 570 the deidentified medical test package 315. Since the collaborator 225 does not have the decryption key 325, the collaborator is unable to decrypt the deidentified medical test package 315. As such, the client device 210B of the collaborator 225 displays 580 the unencrypted portion of the medical test package 310 (e.g., test information and test results) and attributes the deidentified medical test package 315 to an anonymous patient.

In some embodiments, a client device determines if the decryption key 325 is available by attempting to decrypt the encrypted portion of the deidentified medical test package 315. If the decryption succeeds, the client device determines that the decryption key 325 is available. However, if the decryption is not successful, the client device determines that the decryption key 325 is not available.

The deidentification scheme described above enables enhances the security and privacy of the systems handling data including patients' PII, as well as enables various entities to share patients' medical information without compromising the security and privacy of the patients.

For example, by deidentifying the medical test package before being stored, a patient's PII is not accessible to an entity without possession or access to the decryption key associated with the encryption key used for deidentifying the medical test package. Moreover, this added security layer is transparent for entities that do have access to the decryption key as the decryption of the patients' PII can be performed in the background each time the entity with decryption key access attempts to retrieve a medical test package.

Additionally, by deidentifying the medical test packages as described above, a medical test package can be shared with third-party entities that do not have access to the decryption key associated with the encryption key used for deidentifying the medical test package, while maintaining the third-party entities' ability to view information useful (e.g., digital medical images) for making a diagnosis or recommendation for a particular patient, or for conducting large scale medical studies.

B. Volumetric Imaging

The volumetric imaging module 280 receives a request, from a client device, for a new volumetric image and provides a set of images to generate the volumetric image. For example, the volumetric imaging module 280 provides a set of slice images taken across a predetermined plane (e.g., the transverse plane, the sagittal plane, or the frontal plane) to enable the client device to generate a three-dimensional (3D) model using the set of slice images.

In some embodiments, the reduce the amount of data being transmitted to the client device, the set of slice images are compressed prior to being transmitted to the client device. Moreover, to preserve the image quality of the set of slice images, a lossless compression algorithm may be used. Moreover, to increase the efficiency of the compression algorithm, two or more slices are combined into a combined image prior to applying the image compression algorithm.

Figure 6A:
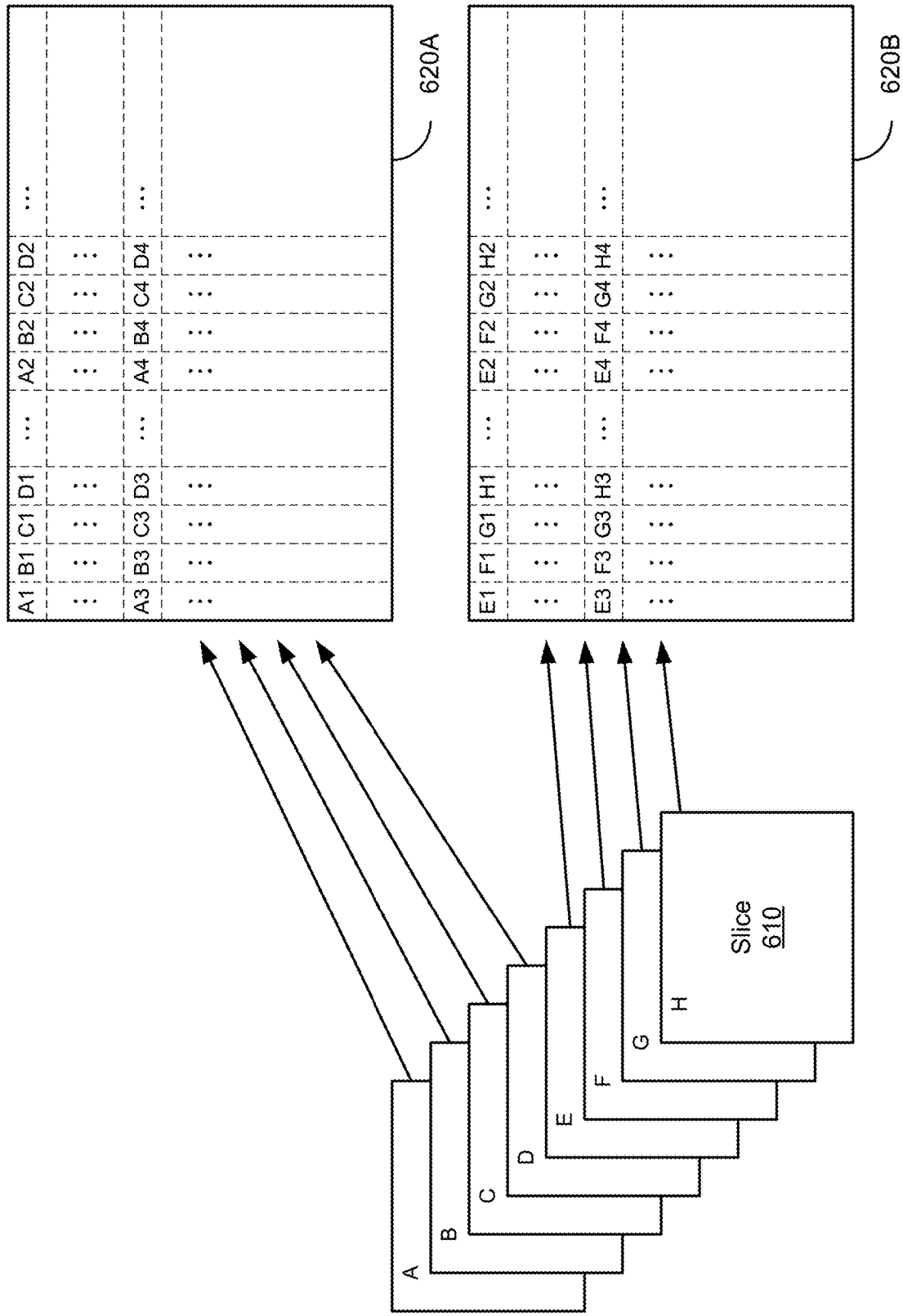
FIGS. 6A and 6B illustrate system environments for the compression of a set of slice images, according to various embodiments.
Figure 6B:
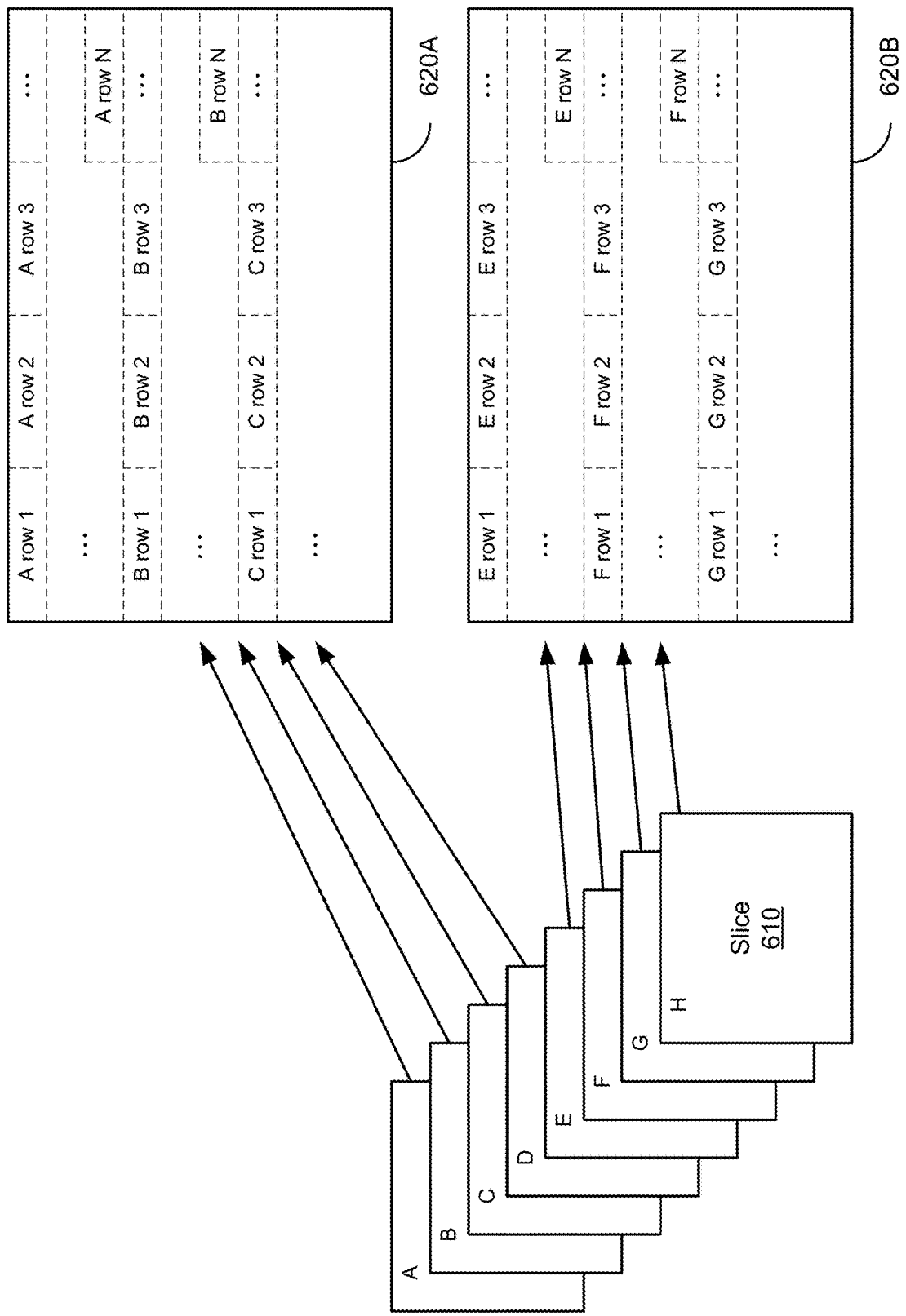
Figure 6C:
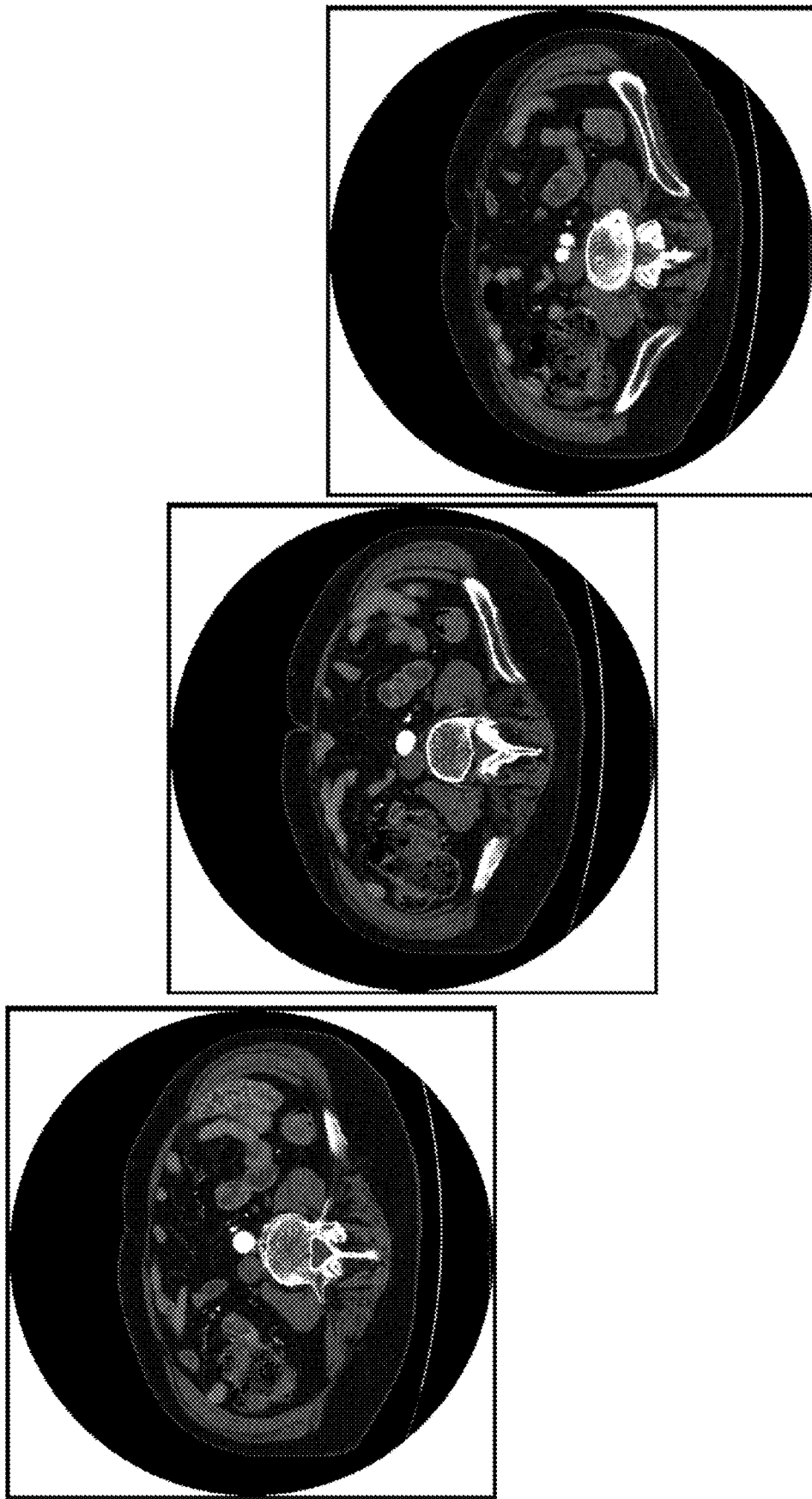
FIG. 6C illustrates an example set of slice images, according to one embodiment.

FIGS. 6A and 6B illustrate system environments for the compression of a set of slice images, according to various embodiments. FIG. 6C illustrates an example set of slice images, according to one embodiment. The system environment of FIGS. 6A and 6B show a set of slice images containing eight images A through H. A first subset of images (e.g., slices A through D) are combined into a first combined image 620A and a second subset of images (e.g., E through H) are combined into a second combined image 620B.

In some embodiments, the number of slices that are combined into a single combined image is determined based on the size of each slice and the capabilities of the client device. For example, the client device might be limited on a maximum image size that it can handle (e.g., based on computational power, available memory, or operating system restrictions). For instance, if the image size limit of the client device is 4096×4096 pixels and each slice is 512×512 pixels, then 64 slices may be combined into a single combined image 620. As such, if the set of slice images include 320 slices (each having a resolution of 512×512 pixels), those slices can be combined into 5 combined images 620.

In some embodiments, as shown in the example of FIG. 6A, the lines or pixels from each of the images used for generating a single combined image are interlaced. For example, to improve the efficiency of the compression, since adjacent slices are similar to each other, the pixels of two or more images are interlaced to reduce the number of sharp changes in the combined image.

Alternatively, as shown in the example of FIG. 6B, to improve the speed of the process, each image is spread horizontally in the combined image 620. For example, if each slice is 512 pixel wide and the combined image is 4096 pixels wide, the pixels in the first 8 rows of the first slice are placed in the first line of the combined image, the second 8 rows of the first slice are placed in the second line of the combined image, and so forth. After all the pixels of the first slice are placed in the combined image, the pixels of the second slice are placed in the placed in the combined image. As such, the combined image can be composed sequentially based on the data for each slice independently.

In some embodiments, to generate a combined image 620, a blank image having a pre-determined size is generated. The pre-determined size may be determined based on the number of slices 610 to be combined and the size of each of the slices 610. Alternatively, the pre-determined size may be a pre-set value. After the blank image is initialized, the pixels of the blank image are modified based on the pixel value of a corresponding pixel of a corresponding slice.

For example, for each pixel of each slice 610 in a subset of slices to be combined into a combined image 620, a corresponding location in the combined image is determined. Then, the pixel value of the blank image at the determined location is modified to match the pixel value of the pixel of the slice. Alternatively, if the bit depth (or color depth) of the combined image is different than the bit depth of the slice, the pixel value of the blank image at the determined location is modify based on a subset of bits of the pixel of the slice.

After the slices have been combined into combined images, the combined images are compressed to reduce the amount of data being transferred to the client device. In some embodiments, the compressed combined images are stored in the content store 275. In other embodiments, the composition of the combined images and the compression of the combined images is performed each time a new request is received from the client device.

In some embodiments, the images are decomposed into multiple resolution planes. For example, each slice may be received as having a 16-bit gray scale color depth. Each slice may be split into two 8-bit gray scale color depth images. The slices can then be combined into two (or more) sets of combined images, each corresponding to resolution plane of slices.

Figure 7A:
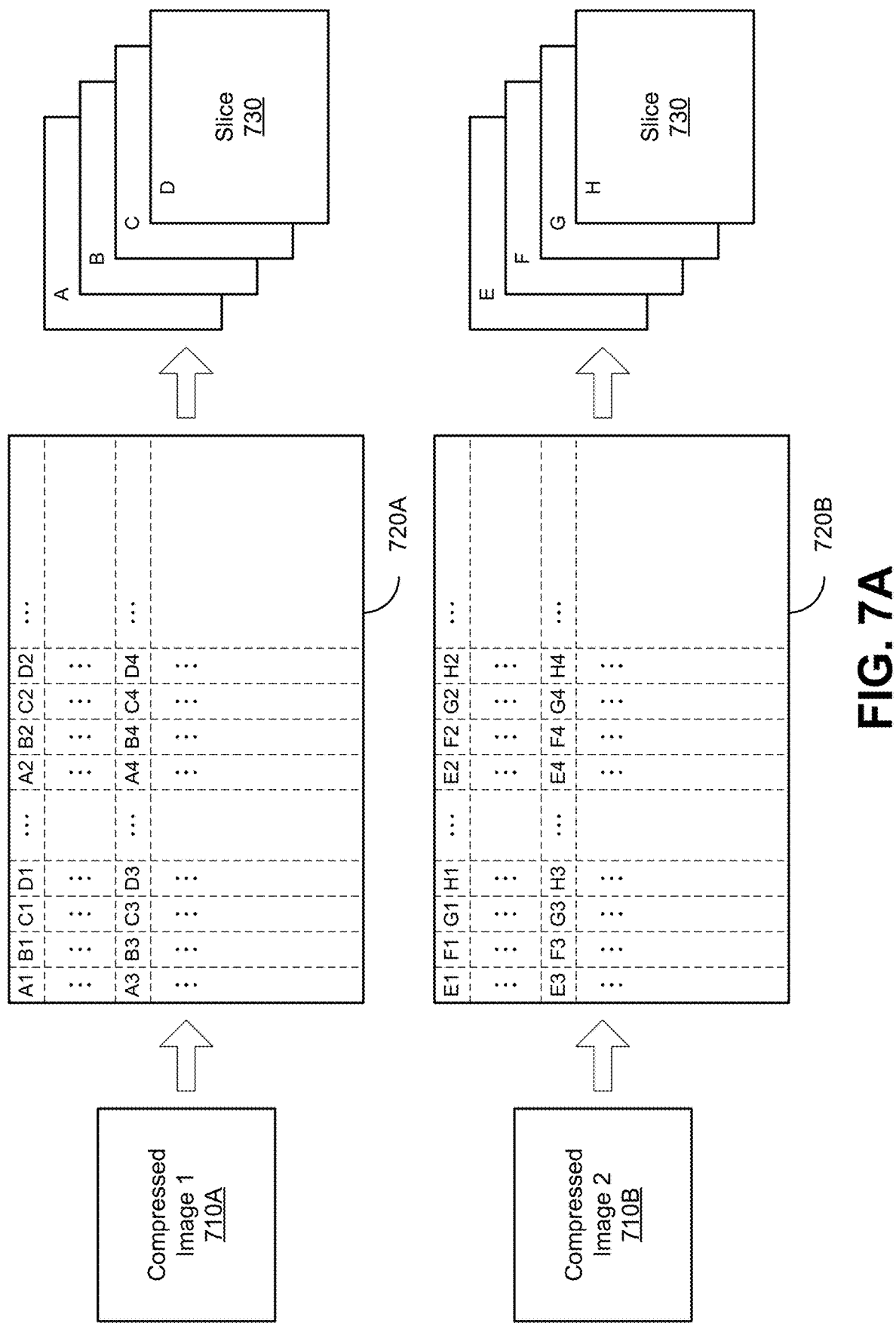
FIG. 7A illustrates a system environment for the decompression of a set of slice images, according to one embodiment.

FIG. 7A illustrates a system environment for the decompression of a set of slice images, according to one embodiment. The system environment of FIG. 7A shows a set of compressed images 710. A first compressed image 710A is then decompressed to obtain a first combined image 720A. Similarly, a second compressed image 710B is decompressed to obtain a second combined image 720B. Although the example embodiment of FIG. 7A only shows two compressed images 710, additional compressed images may be used depending on the number of slices captured by the medical imaging device.

After the compressed images 710 are decompressed, the decompressed combined images 720 are split to generate a set of slices 730. For example, the first decompressed combined image 720A is split into a first subset of slices and the second decompressed combined image 720B is split into a second subset of slices. In some embodiment, additional metadata is provided to specify a set of parameters for splitting the combined images. For example, the set of parameters may include the size of each of the slices to extract from the combined images, or a scheme used to combine the slices to generate the combined image.

In some embodiments, to split each of the decompressed combined images, a set of blank images are first initialized. Then, for each initialized blank image, the pixel values of each of the pixels are determined from one or more decompressed combined images 720. After determining the pixel values, the initialized blank images are modified to store the determined pixel values at predetermined locations of the initialized blank image.

In some embodiments, if the bit depth (or color depth) of the decompressed combined image is the same as the set of slices to be extracted, the pixel values for each pixel of a slice is determined from a single decompressed combined image. In other embodiments, if the bit depth of the decompressed combined image is lower than the set of slices to be extracted, the pixel value for each pixel of a slice is determined from multiple decompressed combined image.

Figure 7B:
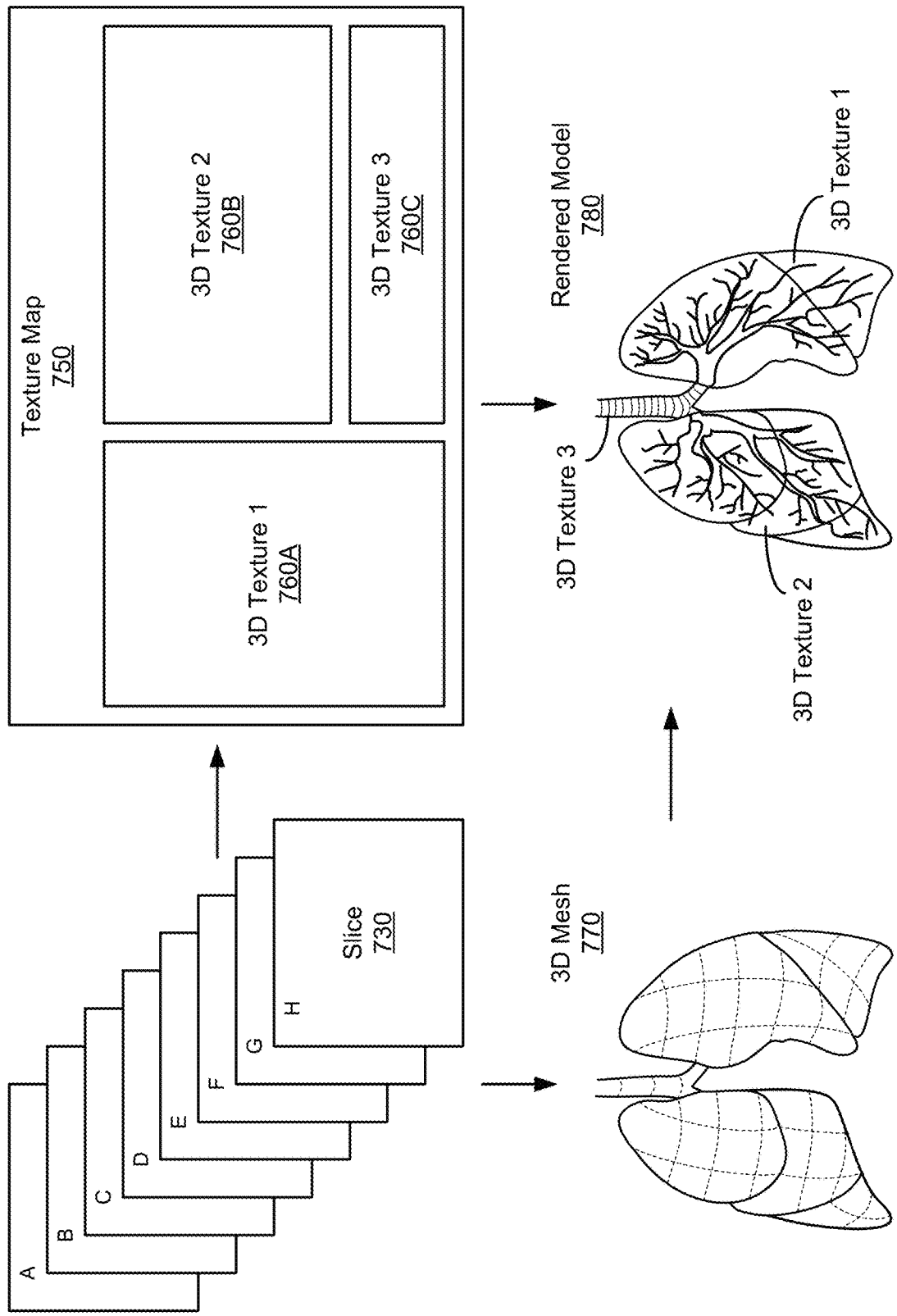
FIG. 7B illustrates a system environment for the generating a three-dimensional (3D) model from a set of slides, according to one embodiment.

FIG. 7B illustrates a system environment for the generating a three-dimensional (3D) model from a set of slides, according to one embodiment. After the slices are extracted from the combined images, the slices are used to generate a texture map 750. The texture map may include one or more textures 760 that is used by a shader to provide high frequency details to the surface of the 3D model.

In some embodiments, the model is also generated from the extracted slices. For example, based on the image in each of the slices, a 3D mesh structure 770 is generated. In some embodiments, vertices for the 3D mesh structure are identified from each of the slices and the vertices are connected to form the 3D mesh structure. The 3D mesh and the texture map are then used to render an image in a display of a client device.

In some embodiments, the client device allows users to interact with the 3D model. For example, the client device allows users to pan, rotate, and zoom the 3D model to enable the user to view the 3D model from different angles and at different levels of detail (LOD). In some embodiments, multiple models at different LODs are generated. Then when rendering an image for displaying to the user, one of the models is selected based on the angle and zoom parameters used for the rendering. For instance, two models, one with a fine meshing, and one with a coarse meshing are generated. When the client device is rendering, one of the two models is selected based on the zoom parameters to either speed up the rendering process (e.g., by using the coarse meshing) or to provide additional levels of details to the user (e.g., by using the fine meshing).

Figure 8:
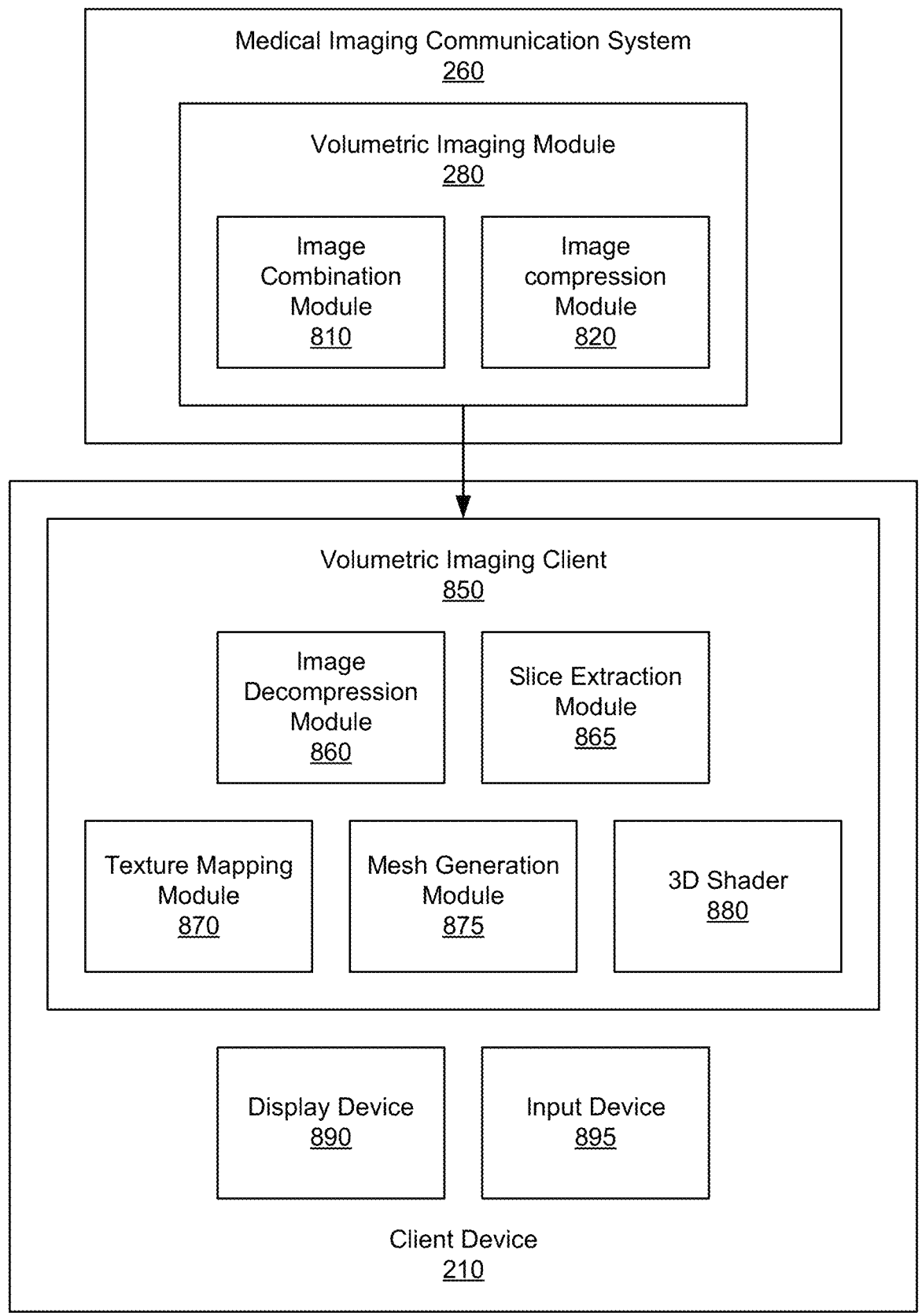
FIG. 8 illustrates a block diagram of the volumetric imaging module of the medical imaging communication system in communication with a volumetric imaging client of a client device, according to one embodiment.

FIG. 8 illustrates a block diagram of the volumetric imaging module 280 of the medical imaging communication system 260 in communication with a volumetric imaging client 850 of a client device 210, according to one embodiment. The volumetric imaging module 280 includes an image combination module 810 and an image compression module 820. The volumetric imaging module 280 communicates with a volumetric imaging client 850 of a client device 210. The volumetric imaging client 850 includes an image decompression module 860, a slice extraction module 865, a texture mapping module 870, a mesh generation module 875, and a 3D shader 880. Moreover, the client device 210 includes a display device 890 and an input device 895.

The image combination module 810 receives a set of slice images (slices) 610 and generates one or more combined images 620. The image combination module 810 selects a subset of slices 610 to combined into a single combined image 620 and arranges the pixels of each of the slices 610 in the subset of slices in the combined image 620.

The image compression module 820 receives one or more combined images 620 and compresses the received combined images. In some embodiments, the image compression module 820 uses a lossless compression algorithm. In some embodiments, the combination of slices by the image combination module 810 is performed in a manner to increase the efficiency of the image compression algorithm used to compress the images. As such, the file size of the compressed combined image is lower than the combined file sizes of the slice images in the subset of slices.

The image decompression module 860 receives one or more compressed combined images 710 and decompresses the compressed combined images to restore the combined images 720. In some embodiments, the image decompression module 860 identifies a compression algorithm used to compress the combined image and applies an inverse operation to the compression algorithm.

The slice extraction module 865 receives a combined image 720 and extracts the slices 730 used to compose the combined image 720. In some embodiments, the slice extraction module 865 identifies a set of parameters for performing the extraction of the slices. For example, the slice extraction module 865 determines a size (e.g., in pixel) of each slice, a number of slices, and an algorithm used to combine the slices.

The texture mapping module 870 receives a set of slices and generates a texture map 750 for rendering a 3D model of the object depicted in the slices. The texture map 750 may include multiple textures 760 that the shader 880 can use to render images of the 3D model. In some embodiments, the texture mapping module 870 generates a set of matrices or vectors based on the pixel information stored in each of the slices. For example, for each slice, the texture mapping module 870 generates a set of vectors that stores the value for each of the pixels of the slice in a specific location within a specific vector of the set of vectors. Alternatively, each vector of the set of vectors generated by the texture mapping module 870 is generated using values for pixels in multiple slices. That is, each vector element in a specific vector may correspond to a pixel for each of a set of slices at a specific location within the corresponding slice.

For example, based on the size of each slice and the number of slices in the set of slices, the texture mapping module initializes a set number of vectors, each having a predetermined size. In some embodiments, the size of the vector is further based on a capability of the computing device executing the texture mapping module 870. For example, the texture mapping module 870 may choose a vector size that is based on the maximum natively supported vector size for the computing device (e.g., based on the capabilities of a graphics processor or the capabilities of the operating system of the computing device). For each vector element of each vector, the texture mapping module 870 stores a value corresponding to a pixel of a specific slice at a specific location.

The mesh generation module 875 receives the set of slices and generates a 3D mesh 770 for rending a 3D model of the object depicted in the slices. In some embodiments, the mesh generation module 875 determines the position of multiple vertices based on each of the slices in the set of slices and connect the vertices to form the 3D mesh. For instance, the mesh generation module 875 may identify edges in each of the slices to determine the position of various surfaces. The mesh generation module 875 then inserts a vertex to the mesh based on the identified location of a surface. Moreover, the mesh generation module 875 connects two or more vertices together to form the 3D mesh. For instance, the mesh generation module 875 connects vertices to form triangles to define the surfaces identified based on the set of slices.

The 3D shader 880 receives the 3D mesh 770 and the texture map 750 and renders the model for display to the user via the display device 790. That is, based on a set of render parameters (e.g., angle, zoom, resolution) the 3D shader 880 generates a 2D image representation of the 3D model and sends the generated 2D image to the display device 790 of the client device 210. In some embodiments, the 3D shader 880 is given a certain budget (e.g., a computational budget and a time budget) and the 3D shader 880 generates the 2D image within the provided budget.

In some embodiments, the rendering parameters are changed based on user input received though the input device 895. The user input may be a touch input on a touch sensitive display, or a pointer input (e.g., a mouse input) using a peripheral connected to the client device. The user input may indicate to change the rendering angle, the rendering zoom, or the resolution of the rendered image. The 3D shader 880 receives the user input or the change in rendering parameters and re-renders the 3D model based on the new rendering parameters.

In some embodiments, the 3D shader 880 generates the 2D image representation of the 3D model without using a 3D mesh. That is, based on the texture map generated by the texture mapping module 870 or directly from the set of slices, the 3D shader 880 determines the 2D image corresponding to a set of rendering parameters. For example, based on a rendering angle, for each pixel of the 2D image, the 3D shader 880 identifies a set of pixels from the texture map or the set of slices and determines a new pixel value by manipulating the values of the identified pixels. If the texture map is a set of vectors or matrices, the 3D shader 880 may manipulate the vectors or matrices of the texture map to generate the 2D image representation of the 3D model at the specified rendering angle.

Figure 9:
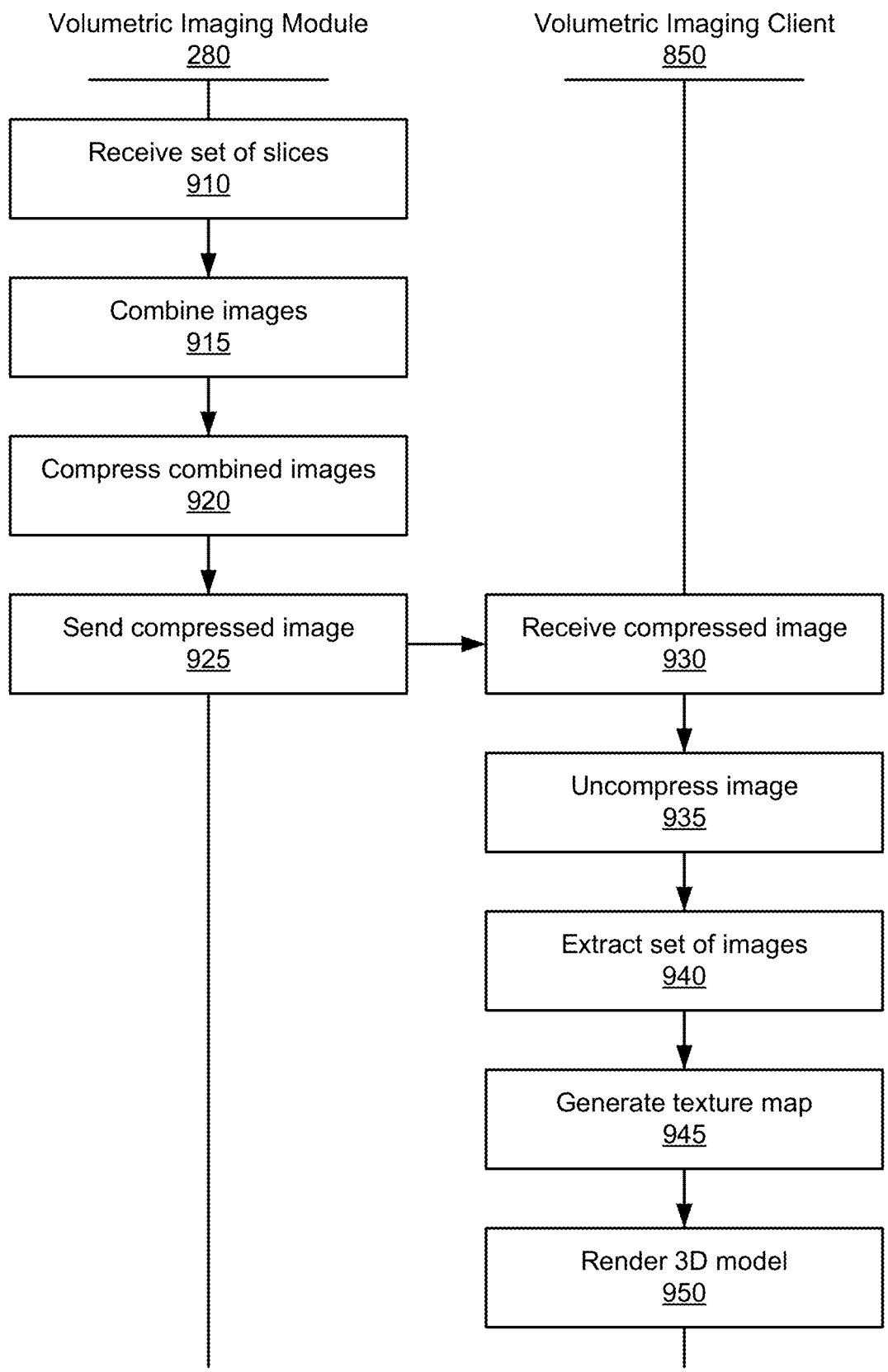
FIG. 9 illustrates a flow diagram of a process for rendering a 3-dimensional image from a set of slice images, according to one embodiment.

FIG. 9 illustrates a flow diagram of a process for rendering a 3-dimensional image from a set of slice images, according to one embodiment. The volumetric imaging module 280 receives 910 a set of slices. In some embodiments, the set of slices are stored in the content store 275. For example, the set of slices may be extracted from deidentified medical test packages 315. In other embodiments, the set of slices are received from other sources, such as a medical imaging device 250 or a third-party online repository.

The image combination module 810 combines 915 the set of slices to generate one or more combined images 620. In some embodiments, the set of combined images are split into multiple subsets of slices and each subset is combined into a single combined image. In other embodiments, each subset is combined into multiple combined images, each containing portions of every slice in the subset of slices. For example, if each slice uses a 16-bit color depth, each combined image may be generated with one half (8 bits) of the color information for each slice in the subset of slices. That is, a first combined image may include the first 8 bits of color information for each slice in the subset of slices, and a second combined image may include the second 8 bits of the color information for each slice in the subset of slices.

The one or more combined images 620 are compressed 920 to generate compressed images 710. In some embodiments, the combined images are compressed using a lossless compression algorithm to prevent any data or resolution loss during the compression process. The compressed images 710 are then sent 925 to a client device 210 (e.g., a provider's 220 client device 210A or a collaborator's 225 client device 210B).

The client device 210 receives 930 the compressed images 710. The image decompression module 860 then decompresses 935 the compressed images 710, and the slice extraction module 865 extracts 940 the set of slices from the uncompressed combined images 720. As such, the information contained in the initial set of slices is transferred from the medical imaging communication system 260 to the client device 210 to a client device (e.g., a mobile device such as a smartphone or a tablet) while reducing the amount of data and bandwidth employed to transfer the set of slices without any loss of information. Moreover, the compressed images 710 enable the set of slices to be transferred between devices faster, increases accessibility and portability of the set of slices.

The texture mapping module 870 generates 945 a texture map 750 from the extracted set of slices. The texture map includes one or more textures for rendering a 3D model of the object depicted in the set of slices. In some embodiments, the mesh generation module 875 generates a 3D mesh 770 from the extracted set of slices. In other embodiments, a pre-generated 3D mesh is selected based on an analysis of the set of slices. In yet other embodiments, the 3D mesh is provided to the client device 210 by the medical imaging communication system 260. In yet other embodiments, a default 3D mesh (e.g., a cylinder, a sphere or a spheroid, a cube, or any other polyhedron or combination thereof) may be used to render the 3D model.

Using the texture map 750 and the 3D mesh 770, the 3D shader 880, renders 950 the 3D model and generates a 2D image for display through a display device 890 of the client device 210. In some embodiments, the shader renders the 3D model based on a set of parameters (e.g., zoom, angle, resolution). Moreover, the user may change the rendering parameters using an input device 895. For instance, the user may interact with the displayed image to rotate the 3D model. Based on the user's interaction, the rendering parameters are modified, and the 3D model is re-rendered. In some embodiments, the rendering parameters are updated in a predetermined way. For instance, the rendering angle changes to display a rotating 3D model to the user.

In some embodiments, the 3D model is periodically re-rendered (e.g., 30 or 60 times per second). In other embodiments, client device executes a rendering loop, where a new rendering cycle starts after a prior rendering cycle ends. In other embodiments, the client device determines if any of the rendering parameters has changed and starts a new rendering iteration when a change in the rendering parameters is detected.

In some embodiments, in addition to rendering a 3D model, the volumetric imaging client 850 is capable of generating slices in a second plane from the slices in a first plane. That is, using the set of slices taken across the first plane (e.g., the transverse plane), the volumetric imaging client is able to determine how slices in any other plane (e.g., the frontal plane or the sagittal plane) would look like. In some embodiments, the new slices are generated directly from the set of slices in the first plane. In other embodiments, the new slices are generated from the 3D model. That is, the new slices are generating by slicing the 3D model into 2D images that are a set distance apart from each other.

In yet other embodiments, the new slices are generated by calculating new pixel values for each of the new slices based on the available slices. That is, for each pixel in a new slice corresponding to the second plane, a set of pixels in the available slices corresponding to the first plane are identified. The volumetric imaging client 850 then computes a new pixel value based on the identified set of pixels from the available slices corresponding to the first plane. For example, for each pixel in a new slice corresponding to a second plane at a set depth, 8 or 9 pixels are identified from one or more slices in the available slices corresponding to the second plane. Based on the identified 8 or 9 pixels, the volumetric imaging client 850 determines the value for the new pixel. This is repeated for each pixel of the new slice. In some embodiments the available slices are stored in one or more matrices or vectors and the new set of slices are generated by manipulating the matrices or vectors based on the angle at which the available slices are being rotated to transform the set of slices from the first plane to the second plane.

For instance, based on the pixel values for each of the slices, a 3D matrix may be generated. Then, based on the 3D matrix, other slices in other plans may be generated. That is, a matrix M[x][y][z] is generated using each of the slices in the set of slices. The matrix is populated by copying the pixel values for a slice into a corresponding plane in the matrix M. That is, the first slice is copied into the matrix elements where z=0, the second slice is copied into the matrix elements where z=1 and so on. Then, a first slice in the sagittal plane is generated by extracting 2D matrices where x=1, a second slice in the sagittal plane is generated by extracting 2D matrices where x=2, and so on. Additionally, a first slice in the frontal plane is generated by extracting 2D matrices where y=1, a second slice in the frontal plane is generated by extracting 2D matrices where y=2, and so on.

Alternatively, the slices in other planes are generated by extracting rows or columns of pixels from each of the slices in the set of slices at a predetermined position. For example, a first slice in the sagittal plane is generated by the first column of pixels in each slice in the set of slices, a second slice in the sagittal plane is generated by the second column of pixels in each slice in the set of slices, and so on. Moreover, a first slice in the frontal plane is generated by the first row of pixels in each slice in the set of slices, a second slice in the frontal plane is generated by the second row of pixels in each slice in the set of slices, and so on.

In some embodiments, interpolation algorithms are used to determine pixel values corresponding to pixels that are in between two slices. Additionally, the interpolation algorithms may be used to smooth out the generated set of slices in across different planes.

By compressing the set of slices as described above, an amount of data to be transferred to a client device to enable the client device to render a 3D model of an object depicted in the slices may be reduced. That is, the amount of data to be sent using the described compression algorithm may be smaller compared to sending a pre-generated 3D model and a pre-generated 3D texture map. In particular, the benefit of transmitting the compressed data as described above increases when the information is to be sent without loss of fidelity. That is, without the use of lossy compression algorithms that can reduce the resolution and fidelity of the image to be displayed by the client device. This benefit is particularly useful when transferring sets of slices to a mobile device via a wireless connection that might get bottlenecked by the large amount of data to be transferred.

Moreover, by sending the set of slices from which a 3D can be generated, as opposed to sending the pre-generated 3D model, the client device is able to provide additional functionality without any additional cost associated with data transfer. For example, the client device is able to generate multiple models with varying levels of detail, generate additional slices across different planes, etc.

C. Visual Reporting

The visual reporting module 285 receives a medical test package 310 or a deidentified medical test package 315 and formats the contents for display by a client device 210. For example, the visual reporting module 285 generates a web page to display the contents of the medical test package. The visual reporting module 285 then sends the formatted content to a client device for display (e.g., through a web browser application).

Figure 10A:
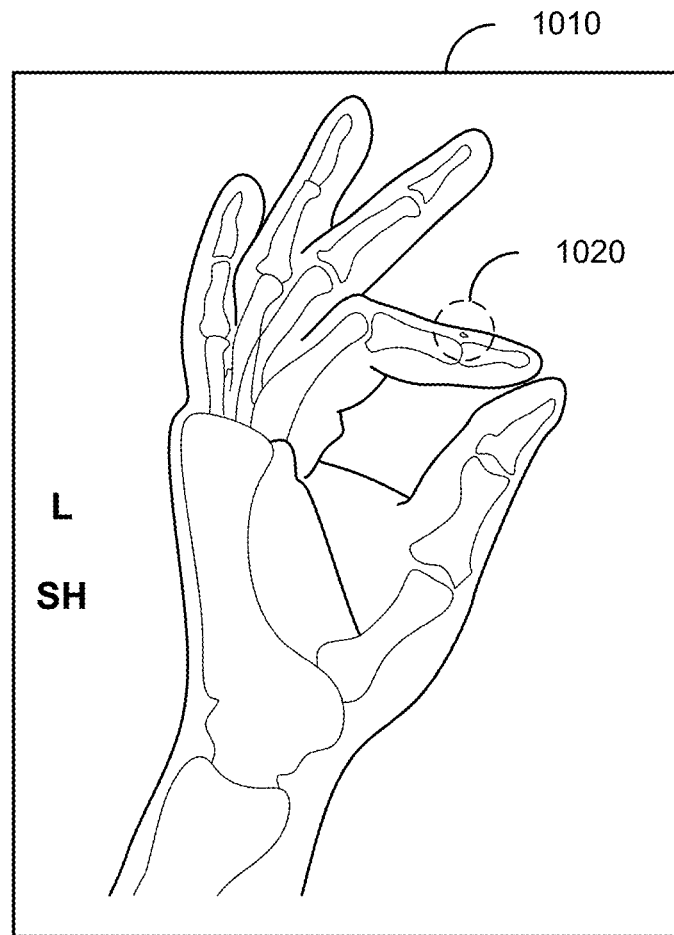
FIG. 10A illustrates a system environment for processing digital medical images in a collaborative way, according to one embodiment.
Figure 10A:
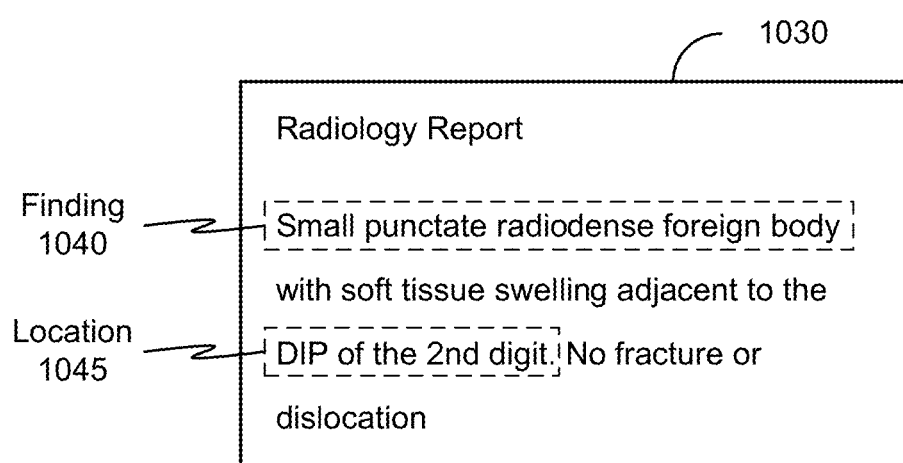

FIG. 10A illustrates a system environment for processing digital medical images in a collaborative way, according to one embodiment. FIG. 10A illustrates a medical image 1010 and a report 1030 for the medical image. The medical image depicted in FIG. 10A corresponds to an X-Ray of the left hand of a patient. However, any other suitable medical image (such as a CT scan, an MRI, or an ultrasound) may also be used. The report 1030 is a radiology report provided by a medical professional after inspecting the medical image 1010. In some embodiments, the report 1030 is provided by a collaborator 225.

The report 1030 includes a description of what the medical professional observed in the medical image. For example, the report 1030 includes a finding 1040 and a location 1045 that corresponds to the finding 1040. In some embodiments, the report 1030 may be automatically generated by the visual reporting module 285 and edited by a medical professional to augment or correct the findings of the visual reporting module 285. In the example of FIG. 10A, the finding is the presence of a small foreign object and the location of the finding is the distal interphalangeal joint (DIP) of the second digit.

In some embodiments, natural language processing (NLP) is used to identify the findings and the locations embedded in the report 1030. In some embodiment, the NLP identifies words related to locations and nouns corresponding to parts of a human body. In other embodiments, the medical professional also provides a location associated with the report. The location is stored in conjunction with the report. For example, the medical professional may specify a point or coordinate (e.g., by clicking a specific point in the medical image), or an area (e.g., by drawing a bounding box or area on the medical image). The visual reporting module 285 then stores the provided location for display to a viewing user.

In some embodiments, based on the description of the location, the visual reporting module 285 finds a coordinate or area on the medical image corresponding to the location 1020. For example, if the location 1045 is "adjacent to the DIP of the 2nd digit," an image recognition model identifies a region of the medical image corresponding to the specified location. In some embodiments, a trained model is used to identify the specified location. For example, a classifier model that scans the medical image using a set of "windows" and determines if any of the windows have a likelihood greater than a threshold value of depicting the specified location.

Figure 10B:
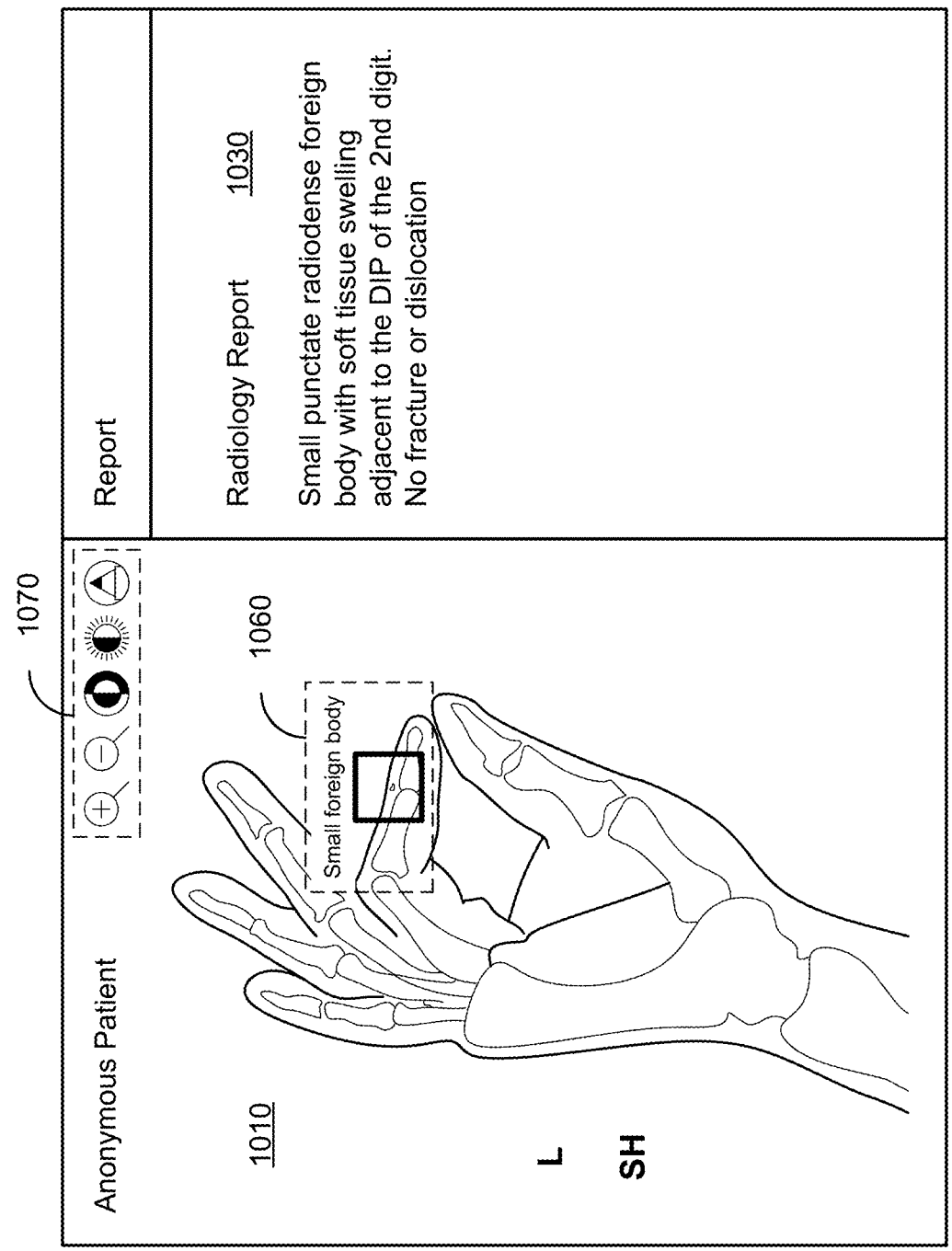
FIG. 10B illustrates a user interface for viewing a medical report corresponding to a medical image, according to one embodiment.

FIG. 10B illustrates a user interface for viewing a medical report 1030 corresponding to a medical image 1010, according to one embodiment. The user interface shows the medical image 1010 and the medical report 1030. The medical image is modified to include an identification 1060 of the finding 1040 at the specified location 1045. Additionally, the user interface may include buttons 1070 to interact with the medical image or the report. For instance, the buttons allow a viewing user to zoom in or out the medical image, or to change the contrast and saturation of the medical image. Moreover, the buttons may allow a viewing user to modify the medical report 1030 or to change the identification 1060 of the location if the system incorrectly determined position corresponding to the location.

In some embodiments, prior to displaying the medical image, the visual reporting module 285 identifies bounding boxes to the medical images and corrects a rotation of the medical images. Moreover, the visual reporting module 285 may equalize the size of multiple medical images to present the medical images as having similar dimensions.

Figure 11:
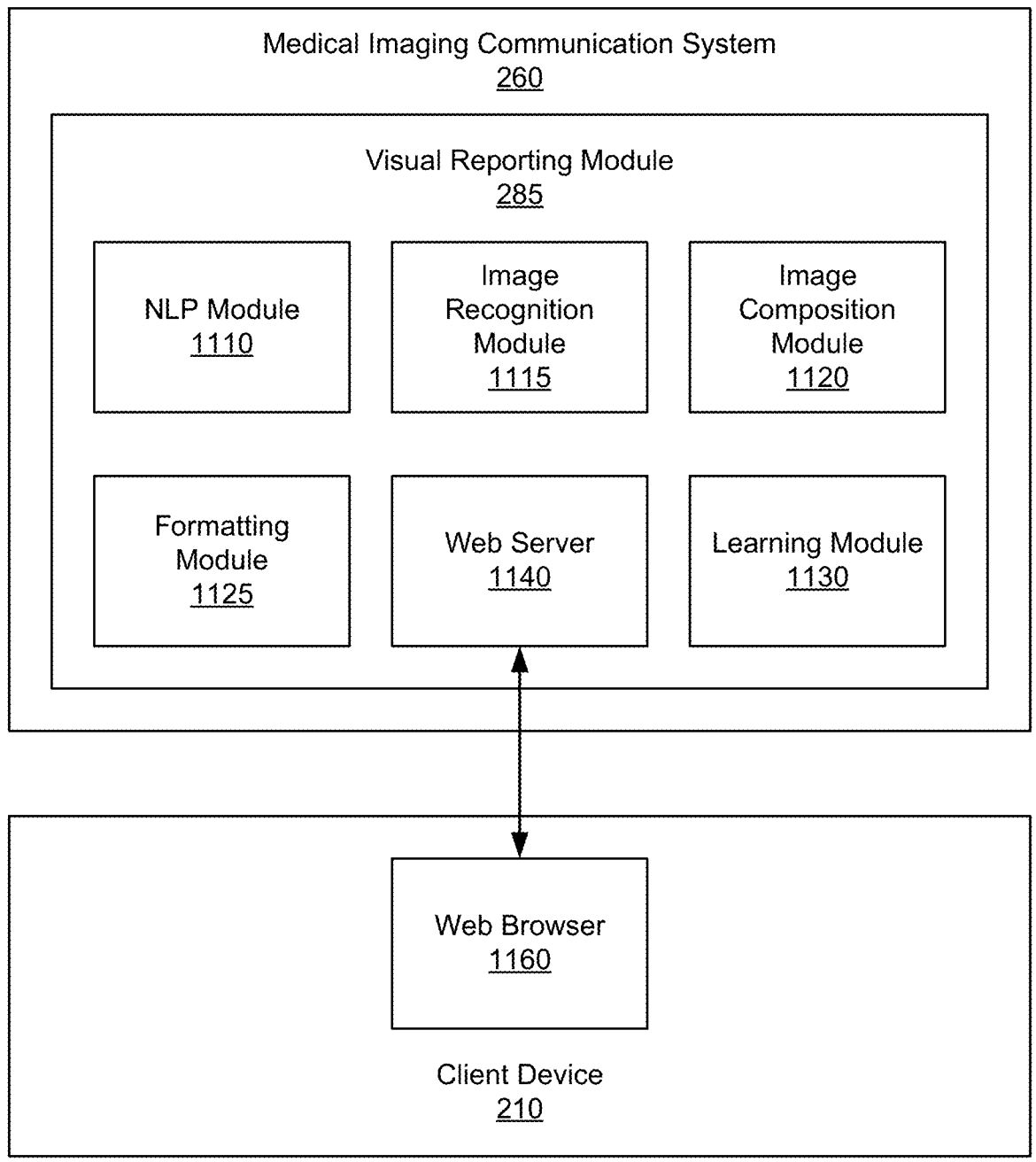
FIG. 11 illustrates a block diagram of the visual reporting module of the medical imaging communication system, according to one embodiment.

FIG. 11 illustrates a block diagram of the visual reporting module of the medical imaging communication system, according to one embodiment. The visual reporting module 285 includes a natural language processing (NLP) module 1110, an image recognition module 1115, an image composition module 1120, a formatting module 1125, a learning module 1130, and a web server 1140.

The NLP module 1110 analyzes written medical reports and extracts one or more pieces of information (e.g., data) from the medical reports. In some embodiments, the NLP module extracts at least a description of a location from the text of the medical reports. The NLP module 1110 uses one or more NLP models to extract the one or more pieces of information. For instance, the NLP module 1110 may include a different model for each type of information to be extracted from the text of the medical report. That is, the NLP module 1110 may include a first NLP model that extracts a description of a location from the text of the medical report, and a second NLP model that extracts a description of the finding of the medical report.

The NLP models of the NLP module 1110 are trained by the learning module 1130. The NLP models may be trained using labeled training data. For instance, the NLP models are trained using medical reports for which the pieces of information to be extracted are manually identified. In some embodiments, the NLP models are updated using user feedback regarding the accuracy of the NLP models. For instance, a user may provide an indication that an output of an NLP model is inaccurate (and provides a correct output for the model). The learning module 1130 may then re-train the NLP model based on the received feedback.

The image recognition module 1115 receives a medical image and identifies one or more objects in the received medical image. In some embodiments, the image recognition module 1115 identifies as many objects as possible. In other embodiments, the image recognition module 1115 identifies one or more specified objects. That is, for each region of the medical image, the image recognition module 1115 determines if the specified object is present or not.

In some embodiment, the image recognition module 1115 uses a rolling window that scans across the medical image. The image recognition module 1115 starts with a window having a predetermined size and determines if an object is present in the window. After analyzing the window, the image recognition module 1115 moves the window and repeats the analysis with the new window. This process is repeated until the entire image has been analyzed. In some embodiments, after the entire image has been analyzed, the size of the window is modified, and the process is repeated with the new window size.

The image recognition module 1115 uses one or more models to identify objects. For example, the image recognition module 1115 may include a separate model to identify each of the objects that are supported by the image recognition module 1115. Each image recognition module may be trained using positive training sets including the object to be recognized. Moreover, each model may provide a score indicative of a likelihood that the object being identified is present. The image recognition module 1115 then compares the output of a model to a threshold value to determine if the object is present.

In some embodiments, the image recognition module 1115 selects a model to apply based on the object to be identified. For instance, if the specified object to be identified is a "DIP of the 2nd digit," the image recognition module 1115 selects a model for identifying interphalangeal joints. Moreover, the image recognition module 1115 may use multiple models to identify a single object. For example, to identify the "DIP of the 2nd digit," the image recognition module 1115 may use a first image recognition model to identify the second digit of a patient in a medical image, and a second image recognition model to identify an interphalangeal joint within the identified portion of the image corresponding to the second digit of the patient.

Additionally, the image recognition module 1115 analyzes medical images and determines a likelihood that one or more abnormalities are present in the medical image. For example, the image recognition module 1115 may be trained to detect foreign objects that are not expected to be present in a specific medical image. The image recognition module 1115 may train a model for each abnormality supported by the image recognition module 1115. Alternatively, the image recognition module 1115 trains a single model that is able to recognize multiple types of abnormalities in a medical image. In some embodiments, the image recognition module 1115 identifies a type of object depicted in the medical image and selects a model to apply to the medical image based on the identified object. For instance, if the identified object is a heart, the image recognition module 1115 applies one or more abnormality detection model that is specific for heart images. Conversely, if the identified object is a lung, the image recognition module 1115 applies one or more abnormality detection model that is specific for lung images.

The image composition module 1120 receives a medical image, and an identified area corresponding to a medical report, and modifies the image to include an indication of the area corresponding to the medical report. For instance, the image composition module 1120 adds a box surrounding the identified area corresponding to the medical report. Moreover, the image composition module 1120 adds a short description of the medical report near the indication of the area corresponding to the medical report.

In some embodiments, the image composition module 1120 additionally modifies the medical image to correct certain properties of the medical image. For instance, the image composition module 1120 may rotate the medical image, may change the saturation and brightness of the medical image, or may change the size or resolution of the medical image.

The formatting module 1125 generates a web page to present a medical test package to a viewing user. That is, formatting module 1125 generates a web page to present the medical image and the medical report to a viewing user. In some embodiments, the formatting module 1125 receives an indication of a user's credentials and determines whether to display a patient's PII or to display the medical test package as being attributed to an anonymous patient. For example, the formatting module 1125 includes the patient's PII if the viewing user is the medical provider 220 of the patient 230, and provides the medical test package as being attributed to an anonymous patient if the viewing user is a collaborator 225.

The learning module 1130 applies machine learning techniques to generate one or more models that when applied to content items output indications of whether the content items have the associated property or properties, such as probabilities that the content items have a particular Boolean property, or an estimated value of a scalar property. As used herein, content items include any type of content, such as medical images or medical reports.

As part of the generation of the models, the learning module 1130 forms a training set of content items by identifying a positive training set of content items that have been determined to have the property in question, and, in some embodiments, forms a negative training set of content items that lack the property in question.

The learning module 1130 extracts feature values from the content items of the training set, the features being variables deemed potentially relevant to whether or not the content items have the associated property or properties. An ordered list of the features for a content item is herein referred to as the feature vector for the content item. In one embodiment, the learning module 1130 applies dimensionality reduction (e.g., via linear discriminant analysis (LDA), principle component analysis (PCA), or the like) to reduce the amount of data in the feature vectors for content items to a smaller, more representative set of data.

The learning module 1130 uses supervised machine learning to train the models, with the feature vectors of the positive training set and the negative training set serving as the inputs. Different machine learning techniques—such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—may be used in different embodiments. The models, when applied to the feature vector extracted from a content item, outputs an indication of whether the content item has the property in question, such as a Boolean yes/no estimate, or a scalar value representing a probability.

In some embodiments, a validation set is formed of additional content items, other than those in the training sets, which have already been determined to have or to lack the property in question. The learning module 1130 applies the trained model to the content items of the validation set to quantify the accuracy of the models. Common metrics applied in accuracy measurement include: Precision=TP/(TP+FP) and Recall=TP/(TP+FN), where precision is how many the models correctly predicted (TP or true positives) out of the total it predicted (TP+FP or false positives), and recall is how many the models correctly predicted (TP) out of the total number of content items that did have the property in question (TP+FN or false negatives). The F score (F-score=2*PR/(P+R)) unifies precision and recall into a single measure. In one embodiment, the learning module 1130 iteratively re-trains the models until the occurrence of a stopping condition, such as the accuracy measurement indication that the model is sufficiently accurate, or a number of training rounds having taken place.

The web server 1140 links the visual reporting module 285 via the network 220 to the one or more client devices 210. The web server 1140 serves web pages, as well as other content, such as JAVA®, FLASH®, XML and so forth. In some embodiment, the content provided by the web server is provided by the formatting module 1125 in response to a request received from a client device 210. The web server 1140 may receive and route messages between the visual reporting module 285 and the client device 210. A user may send a request to the web server 1140 to upload information (e.g., comments for a medical test package) that are stored in the content store 275. Additionally, the web server 1140 may provide application programming interface (API) functionality to send data directly to native client device operating systems, such as IOS®, ANDROID™, or BlackberryOS.

The client device 210 may executes a web browser application 1160 to enable interaction between the client device 210 and the visual reporting module 285 via the network 220. Alternatively, a client device 210 interacts with the visual reporting module 285 through an application programming interface (API) running on a native operating system of the client device 210, such as IOS® or ANDROID™. The web browser 1160 receives the web pages provided by the web server 1140, interprets the web pages, and causes the web pages to be displayed through a display device of the client device 210.

Figure 12:
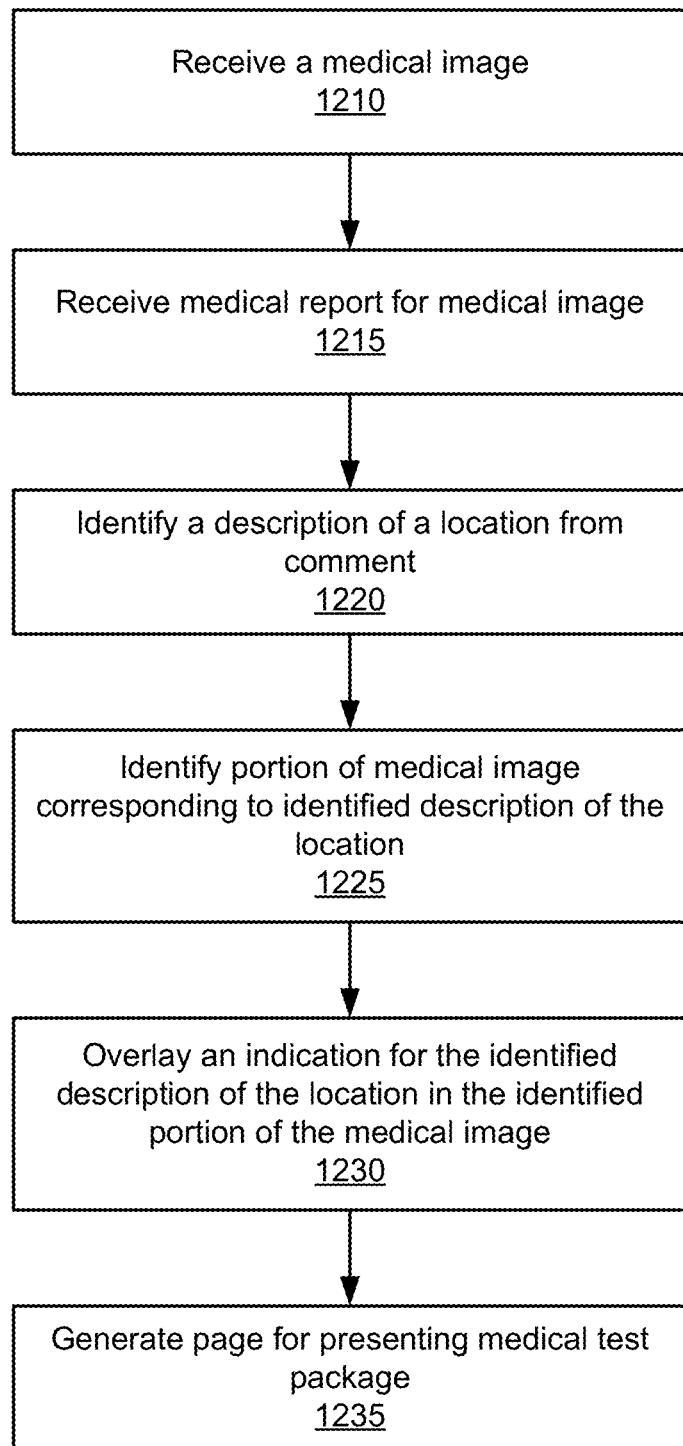
FIG. 12 illustrates a flow diagram of a process for providing collaborative reports of a digital medical image, according to one embodiment.

FIG. 12 illustrates a flow diagram of a process for providing collaborative reports of a digital medical image, according to one embodiment. The visual reporting module 285 receives 1210 a medical image. Additionally, the visual reporting module 285 receives 1215 a medical report for the medical image. In some embodiments, the medical image and the medical report are stored in the content store 275 of the medical imaging communication system 260.

The NLP module 1110 identifies one or more pieces of information form the received medical report. For example, the NPL module 1110 identifies 1220, from the received medical report, a description of a location within the medical image. In some embodiments, the NLP module 1110 further identifies, from the received medical report, a finding associated with the identified description of the location.

The image recognition module 1115 identifies 1225 a portion of the medical image corresponding to the identified description of the location. In some embodiments, the image recognition module 1115 selects an image recognition model based on the identified description of the location and applies the image recognition model to the medical image to identify a portion of the image corresponding to the identified description of the location.

The image composition module 1120 overlays 1230 an indication of the location in the identified portion of the medical image. For example, the image composition module 1120 overlays a bounding box identifying the portion of the medical image corresponding to description of the location included in the medical report.

The formatting module 1125 generates 1235 a page for presenting the medical test package and sends the generated page to a viewing user. The generated page includes the medical image generated by the image composition module 1120 and the text of the medical report.

This process enhances the presentation of digital medical images and the result of an analysis performed to the digital medical images. By annotating the images based on the analysis of the report for the image, a viewing user is able to more easily understand the meaning or significance of the report. Moreover, the annotation process describes above enables a system to store the original digital medical image without having to store multiple versions of the same digital medical image. That is, the system is able to provide the annotated images without having to store a version of the digital medical image that has the annotation baked into it.

Figure 13:
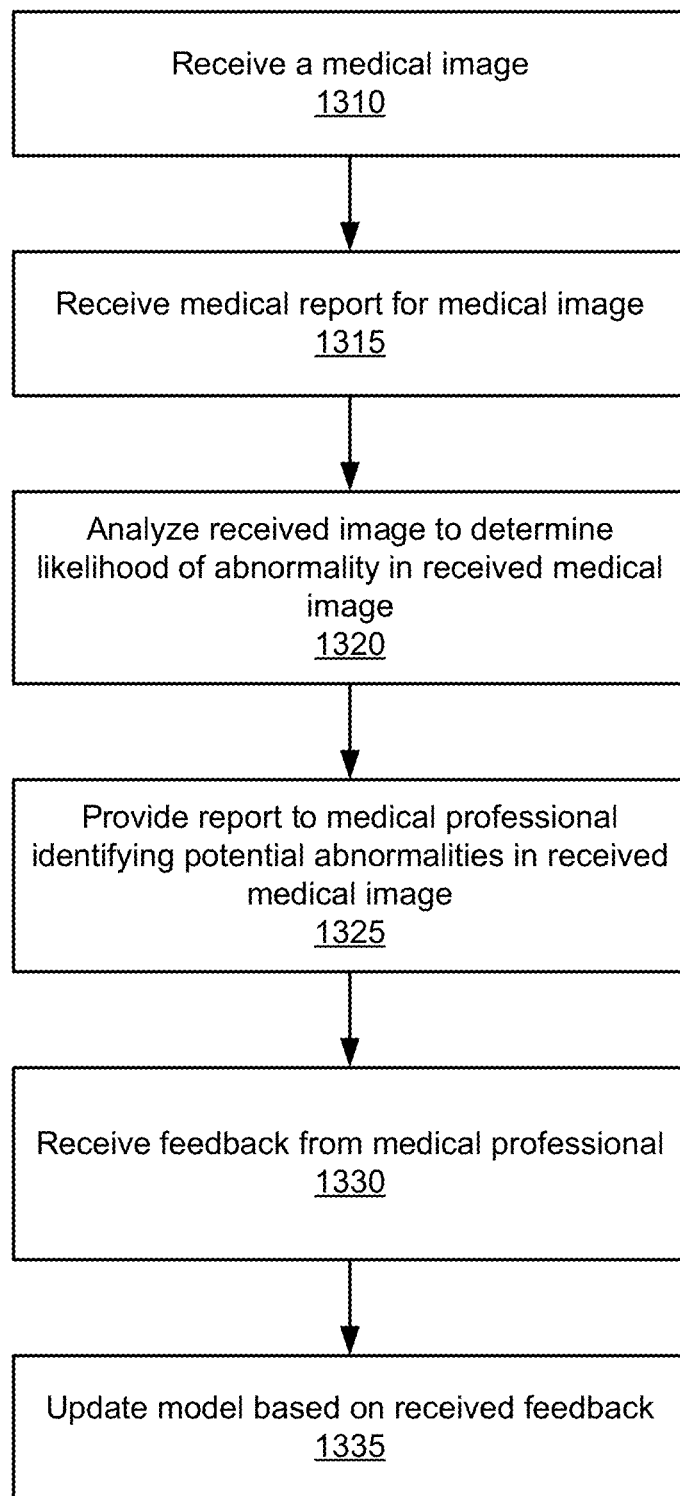
FIG. 13 illustrates a flow diagram of a process for providing an automated analysis of medical images, according to one embodiment.

FIG. 13 illustrates a flow diagram of a process for providing an automated analysis of medical images, according to one embodiment. The visual reporting module 285 receives 1310 a medical image. Additionally, the visual reporting module 285 may receive 1315 a medical report for the medical image prepared by a medical professional.

The image recognition module 1115 analyzes 1320 the received image to determine a likelihood that the received image shows an abnormality. In some embodiments, the image recognition module 1115 first identifies a type of object depicted in the received medical image, and applies one or more models corresponding to the identified type of object. For instance, each model applied may correspond to a type of abnormality that is applicable to the identified type of object.

In some embodiments, the image recognition module 1115 analyzes the received image based on the contents of the received medical report (if one is received). For example, the received medical report may identify the type of object and a region that is suspected to contain an abnormality. As such, the image recognition module 1115 applies one or more models based on the contents of the medical report. Alternatively, the medical report may indicate a suspected abnormality and the image recognition module 1115 applies a corresponding model to determine a likelihood that the suspected abnormality (or a related abnormality) is present in the medical image.

To configure the analysis of the image recognition module 1115 based on the contents of the medical report, the medical report is analyzed using the NLP module 1110. The NLP module 1110 extracts relevant information from the received medical report and provides the extracted information to the image recognition module 1115.

Based on the analysis of the received medical image, an automated report is generated and provided 1325 to a medical profession. The automated report identifies any abnormality having a likelihood higher than a threshold value. In some embodiments, the threshold value is set by the medical professional.

In some embodiments, feedback is received 1330 from the medical professional after the automated report is presented to the medical professional. For example, the medical professional may edit the automated report, may mark portions of the automated report as inaccurate, or may approve the automated report. Based on the feedback received from the medical professional, one or more models used for analyzing the medical image are re-trained and updated.

Additional Configuration Consideration

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method comprising:
    receiving a set of images, wherein each image has a first bit depth and corresponds to a slice of a three-dimensional object;
    combining a first subset of the set of images into a first combined image having a second bit depth lower than the first bit depth, wherein combining the first subset of the set of images comprises:
        for each pixel of each image in the first subset of the set of images:
            determining a location in the first combined image associated with the pixel using a pixel arrangement configured to increase an efficiency of a lossless image compression algorithm;
            determining a new pixel having the second bit depth different from the pixel having the first bit depth; and
            storing the new pixel in the first combined image at the location in the first combined image associated with the pixel;
    combining a second subset of the set of images into a second combined image, the second combined image comprising pixels having the second bit depth;
    compressing the first combined image and the second combined image using the lossless image compression algorithm; and
    transmitting the compressed first combined image and the second compressed second combined image to a client device.

2. The method of claim 1, wherein combining the first subset of the set of images into the first combined image comprises:
    interlacing images in the first subset of the set of images.

3. The method of claim 1, further comprising:
    combining images in the first subset of the set of images into a third combined image, wherein the first combined image and the third combined image have the second bit depth.

4. The method of claim 1, wherein the new pixel having the second bit depth comprises a subset of bits of the pixel having the first bit depth.

5. The method of claim 1, wherein the set of images are medical images captured using a medical imaging device.

6. The method of claim 5, wherein the medical imaging device is one of a computer tomography (CT) scanner, a magnetic resonance imaging (MRI) scanner, an X-ray machine, and an ultrasound machine.

7. The method of claim 1, wherein the set of images are received using a Digital Imaging and Communication in Medicine (DICOM) standard.

8. The method of claim 1, wherein a slice is a two-dimensional image of the three-dimensional object across a specific plane at a specific depth.

9. The method of claim 1, wherein the first subset of the set of images includes images corresponding to a first portion of the three-dimensional object, and wherein the second subset of the set of images includes images corresponding to a second portion of the three-dimensional object.

10. A method comprising:
    receiving one or more compressed combined images, each compressed combined image generated by combining a plurality of images, each image corresponding to a slice of a three-dimensional object and having a first bit depth, wherein each compressed combined image is generated from at least of the plurality of images combined by:
        determining a location in the first combined image associated with each pixel of the plurality of images using a pixel arrangement configured to increase an efficiency of a lossless image compression algorithm;
        determining a new pixel having a second bit depth different from the pixel having the first bit depth; and
        storing the new pixel in the first combined image at the location in the first combined image associated with the pixel;
    decompressing the received one or more compressed combined images to generate one or more decompressed combined images;
    for each of the one or more decompressed combined images:
        extracting, from the decompressed combined image, the plurality of images;
        generating, from the extracted plurality of images, a texture map for a three-dimensional model; and
        rendering the three-dimensional model using the generated texture map.

11. The method of claim 10, wherein extracting the plurality of images comprises:
    extracting a first subset of images from a first decompressed combined image; and
    extracting a second subset of images from a second decompressed combined image.

12. The method of claim 10, wherein extracting the plurality of images comprises:
    deinterlacing the one or more decompressed combined images.

13. The method of claim 10, wherein each decompressed combined image of the one or more decompressed combined images has the second bit depth.

14. The method of claim 10, wherein extracting the plurality of images comprises:
- extracting a first image of the plurality of images, the extraction comprising:
  - for each pixel of the first image, determining a first subset of bits from a pixel of a first decompressed combined image, and determining a second subset of bits from a pixel of a second decompressed combined image.

15. The method of claim 10, further comprising:
- generating, from the extracted plurality of images, a three-dimensional mesh for the three-dimensional model.

16. The method of claim 15, wherein generating the three-dimensional mesh comprises:
- determining a set of vertices from each image of the extracted plurality of images; and
- connecting subsets of the set of vertices to form the three-dimensional mesh.

17. The method of claim 10, wherein the plurality of images are medical images captured using a medical imaging device.

18. The method of claim 17, wherein the medical imaging device is one of a computer tomography (CT) scanner, a magnetic resonance imaging (MRI) scanner, an X-ray machine, and an ultrasound machine.

19. The method of claim 10, wherein a slice is a two-dimensional image of the three-dimensional object across a specific plane at a specific depth.

\* \* \* \* \*

UNITED STATES PATENT AND TRADEMARK OFFICE
CERTIFICATE OF CORRECTION

PATENT NO. : 11,664,115 B2
APPLICATION NO. : 17/106015
DATED : May 30, 2023
INVENTOR(S) : Kevin Quennesson It is certified that error appears in the above-identified patent and that said Letters Patent is hereby corrected as shown below:

In the Claims

In Column 32, in Claim 10, Line 35, delete "least of" and insert -- least one of --, therefor.

Signed and Sealed this
Twenty-fourth Day of October, 2023

Katherine Kelly Vidal
*Director of the United States Patent and Trademark Office*